US006689416B2

United States Patent
Delzer et al.

(10) Patent No.: US 6,689,416 B2
(45) Date of Patent: Feb. 10, 2004

(54) SYSTEM AND METHOD FOR FEEDBACK CONTROL OF AN ABSORBENT CORE MANUFACTURING PROCESS

(75) Inventors: Troy Delzer, Butler, PA (US); John Walter, Renfrew, PA (US)

(73) Assignee: Paragon Trade Brands, Inc., Norcross, GA (US)

( * ) Notice: Subject to any disclaimer, the term of this patent is extended or adjusted under 35 U.S.C. 154(b) by 43 days.

(21) Appl. No.: 10/054,951

(22) Filed: Jan. 25, 2002

(65) Prior Publication Data

US 2003/0143324 A1 Jul. 31, 2003

(51) Int. Cl.[7] ................................................. B05D 1/12
(52) U.S. Cl. ...................................... 427/180; 427/201
(58) Field of Search ................................ 427/180–200, 427/174–176; 118/694, 696–698, 308, 22, 57; 222/238; 209/315, 381, 382

(56) References Cited

U.S. PATENT DOCUMENTS

| | | | | |
|---|---|---|---|---|
| 3,931,787 A | * | 1/1976 | Kuttner et al. | |
| 4,087,506 A | * | 5/1978 | Cook et al. | |
| 4,243,696 A | * | 1/1981 | Toth | 427/474 |
| 5,102,690 A | * | 4/1992 | Iyer et al. | |
| 5,656,325 A | * | 8/1997 | Wallace | |
| 6,143,374 A | * | 11/2000 | Cairncross et al. | 427/533 |
| 2003/0135176 A1 | * | 7/2003 | Delzer et al. | 604/368 |

* cited by examiner

Primary Examiner—Fred J. Parker
(74) Attorney, Agent, or Firm—Hunton & Williams

(57) ABSTRACT

A system and a method for providing feedback control of the deposition of superabsorbent particles into an absorbent core at a specified rate are disclosed herein. A control system, such as a programmable logic control device, is used to receive feedback related to the operation of one or more elements of a vibratory feeder. Based on the feedback, the control system adjusts one or more elements of the vibratory feeder to synchronize the operation of the elements of the vibratory feeder. Particularly, the control system can be adapted to synchronize the deposition rate of superabsorbent particles into the absorbent core with the line speed of the absorbent core during ramp-up and ramp-down periods. Based on a predetermined line speed response during the ramp-up or ramp-down period, the control system can control one or more properties of the vibratory motion of a vibrator of the vibratory feeder in such a manner that the deposition rate of superabsorbent particles is proportional to the line-speed of the fibrous material being supplied so that a substantially uniform concentration of superabsorbent materials are deposited in the absorbent core during the ramp-up and ramp-down periods.

18 Claims, 14 Drawing Sheets

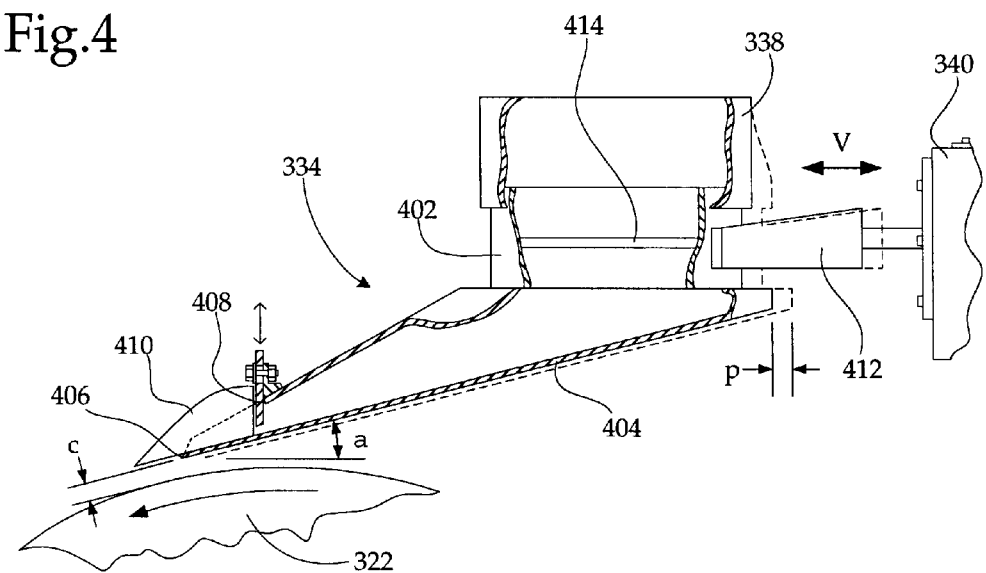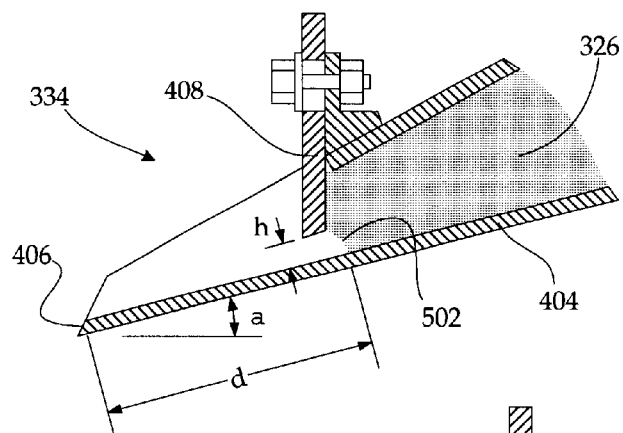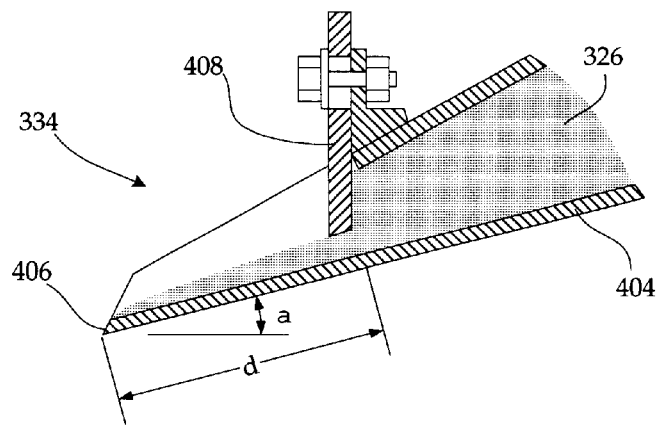

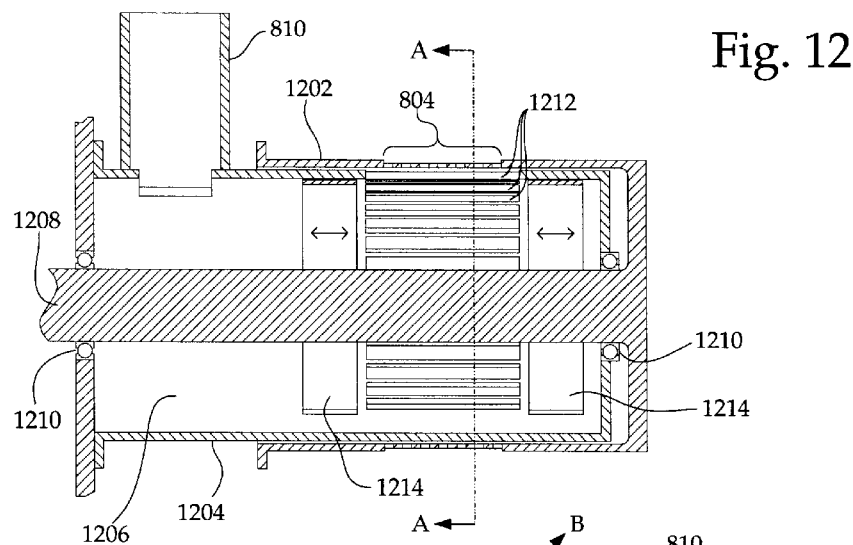
Fig. 12
Fig. 13
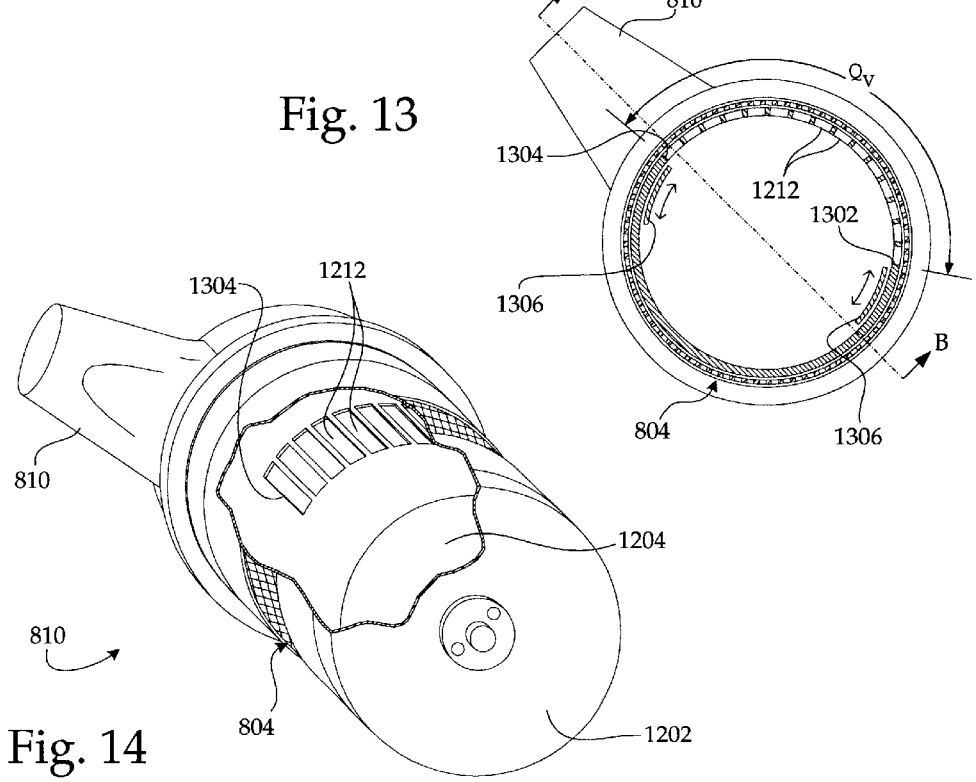
Fig. 14

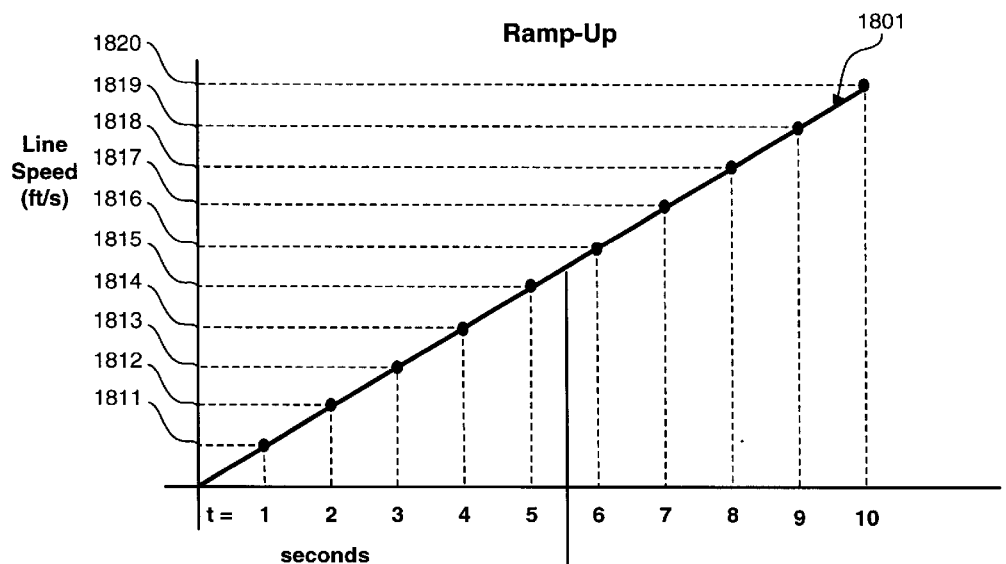
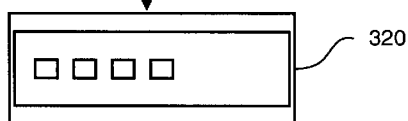
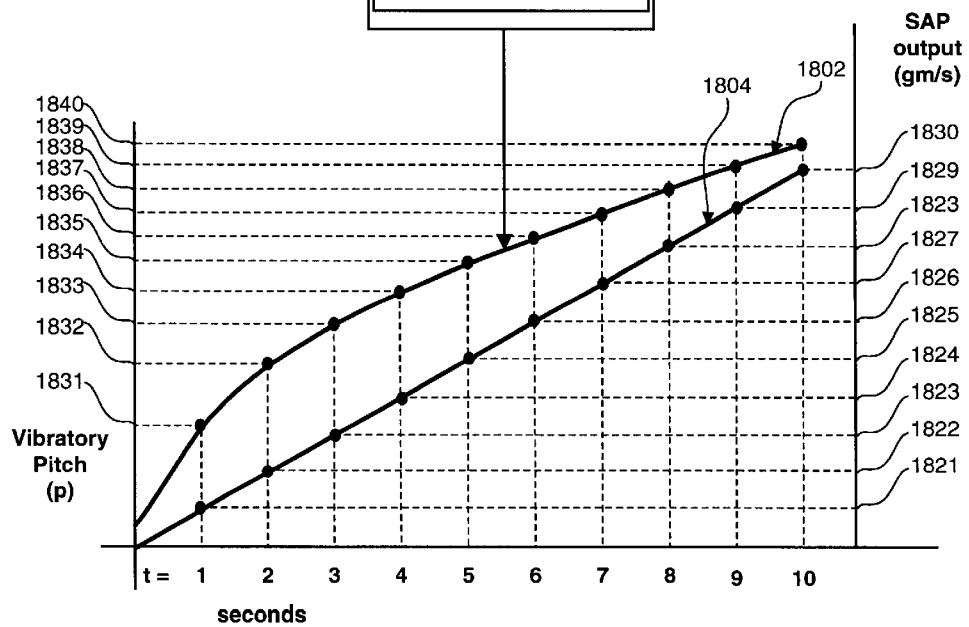
Fig. 18

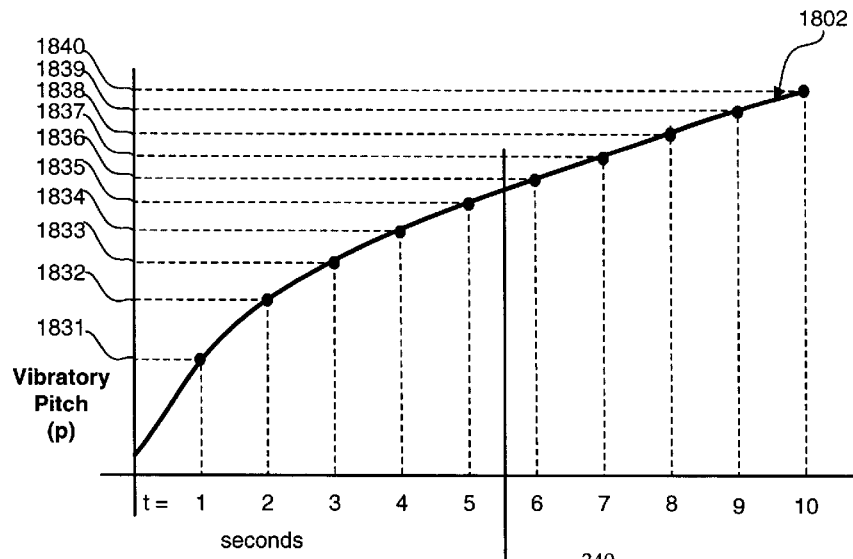
Fig. 19
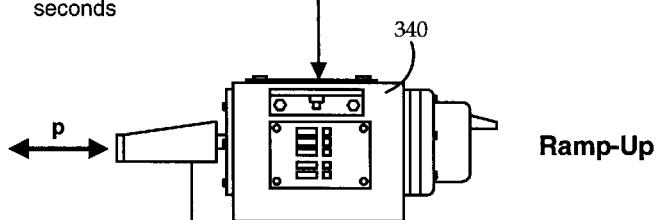
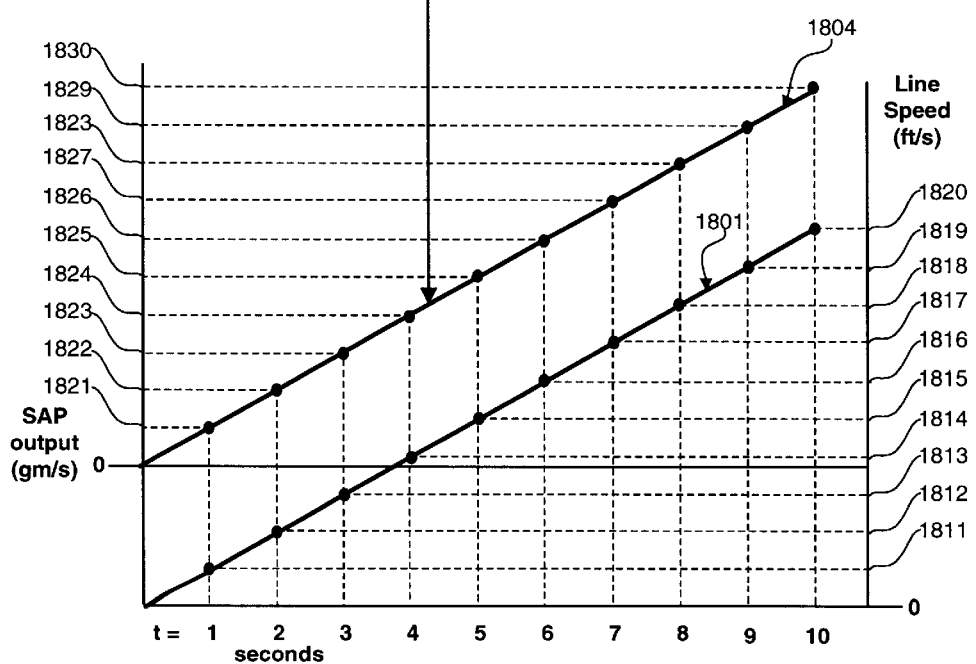

SYSTEM AND METHOD FOR FEEDBACK CONTROL OF AN ABSORBENT CORE MANUFACTURING PROCESS

FIELD OF THE INVENTION

The present invention relates generally to systems and methods for manufacturing absorbent garment cores. More specifically, the present invention relates to a system and method for providing feedback control for the deposition of superabsorbent particles and other particulate and fibrous additives into a dry-formed, absorbent core material.

BACKGROUND OF THE INVENTION

A continuing problem with the manufacture of high integrity tow-based fibrous cores has been to provide the SAP into the fibrous web in a controlled manner. Typical known processes for creating a conventional fluff pulp/SAP core use a large forming chamber to blend the SAP with the fluffed pulp, then convey this blend onto a drum or screen by using a vacuum. The drum or screen has forming pockets that form the fluff pulp/SAP material into the desired shape and the formed cores then are deposited for integration into absorbent products. Such methods have been found to be inefficient during startup and transitions in the manufacturing line speed because they require a relatively large amount of time to provide a stabilized mixture of SAP and fluff pulp, leading to the creation of a large number of scrap products until stabilization.

Other feeding systems use fixed-size moving mechanical gates that provide a uniform amount of SAP to the absorbent core, such as is disclosed in U.S. Pat. No. 6,139,912 to Onuschak et al., which is incorporated herein by reference in its entirety and in a manner consistent with the present invention. Although such devices may be suitable for providing an even flow of SAP or other powdered and particulate additives to absorbent cores, they rely on relatively complex feeding machinery, including a rotary valve that uses a pneumatic SAP conveyor to return undistributed SAP back to a supply container. Pneumatic conveyors typically require a relatively long time to become pressurized and to convey the SAP, causing inefficiencies during transitional phases, such as when the machine operating speed varies, such as during start-up and shut-down, or when it is desired to change the amount of SAP being fed to the core. The additional parts of such feeders may also be expensive and subject to wear and other service problems. Similar devices, having similar deficiencies, are disclosed in U.S. Pat. No. 4,800,102 to Takada, which is incorporated herein by reference in its entirety and in a manner consistent with the present invention.

Still other feeding systems use pneumatic particle projectors that use pressurized gas to convey the SAP to the surface of the absorbent core. Such devices are disclosed, for example, in U.S. Pat. No. 5,614,147 to Pelley and U.S. Pat. No. 5,558,713 to Siegfried et al., which are incorporated herein by reference in their entirety and in a manner consistent with the present invention. Such systems rely on relatively complex air conveyors, that may be susceptible to blockage and may not efficiently accommodate as wide a variety of particulate, powder and fibrous materials as other systems due to their relatively small passage sizes. Such systems may also require a relatively long time to stabilize, leading to inefficiencies during transitional phases.

However, such feeding systems have a number of shortcomings. First, the mixture still is subject to local concentrations and shortages of SAP, often resulting in a rejection of a considerable amount of the material during quality assurance processes. Second, such feeding systems cannot be controlled accurately enough to provide concentrations and shortages of SAP when they are desired.

Another shortcoming often inherent to known feeding systems is that such feeding systems typically can not be accurately controlled to accurately provide reduced SAP amounts that are necessary during transitional phases, leading to cores having undesirable concentrations of SAP manufactures during these transitional phases of operation. Typical known methods and systems to control the amount of SAP provided during these transitional phases generally are unable to adapt the deposition rate of SAP to the changing speeds of these transitional phases. Likewise, the devices used in these feed back systems often are vendor-dependent and therefore are difficult to adapt, if at all, to different operations of these feeding systems.

These are just a few of the disadvantages of the prior art that the preferred embodiments seek to address.

SUMMARY OF THE INVENTION

It would be desirable to provide an apparatus and method for depositing particulate matter, such as superabsorbents, into an absorbent core whereby the amount and position of the additives can be controlled with relative accuracy. It also would be desirable for such an apparatus and method to be able to deposit particulate matter in a manner that fewer rejected products are manufactured during transitional phases, such as startup, stopping and assembly line speed changes. Still further, it would be desirable for such an apparatus and method to be efficient, easy to operate, and capable of operating at high line speeds.

In accordance with these and other features of various embodiments of the invention, a system for synchronizing a deposition of particulate matter into a supply of fibrous material during a transition in a line speed of the fibrous material is provided. The system includes a feed tray having an outlet positioned above the supply of fibrous material, and a vibrator coupled to the feed tray for vibrating the feed tray, wherein when the vibrator vibrates the feed tray particulate matter in the feed tray is deposited onto the supply of fibrous material at a deposition rate substantially proportional to a vibratory motion of the vibrator and when the vibrator does not vibrate the feed tray substantially no particulate matter in the feed tray is deposited onto the supply of fibrous material. The system further includes a programmable logic controller coupled to the vibrator, wherein the programmable logic controller is adapted to control the vibratory motion of the vibrator to affect a transition in the deposition rate that is substantially proportional to the transition in the line speed.

These and other features of the invention will be readily apparent from the Detailed Description that follows, along with reference to the drawings appended hereto.

BRIEF DESCRIPTION OF THE DRAWINGS

FIG. 4 is a partially cut away elevational view of a feed tray according to a preferred embodiment of the present invention, shown at one end of its range of movement and showing the other end of its range of movement in dashed lines;

FIG. 5A is a cut away view of a portion of a feed tray according to a preferred embodiment of the present invention;

FIG. 5B is a cut away view of a portion of another feed tray according to a preferred embodiment of the present invention;

FIG. 12 is an isometric view of yet another combining drum according to a preferred embodiment of the present invention;

FIG. 13 is a cross sectional view of a combining drum assembly according to a preferred embodiment of the present invention as viewed from a direction orthogonal to the rotating axis of the combining drum, and as seen from reference line BB of FIG. 14;

FIG. 14 is a cross sectional view of the combining drum assembly of FIG. 13, as seen from reference line AA;

FIGS. 18 and 19 are charts illustrating a method for controlling a rate of deposition of superabsorbent particles during a ramp-up period in accordance with a preferred embodiment of the invention.

DETAILED DESCRIPTION OF THE PREFERRED EMBODIMENTS

Figure 1:
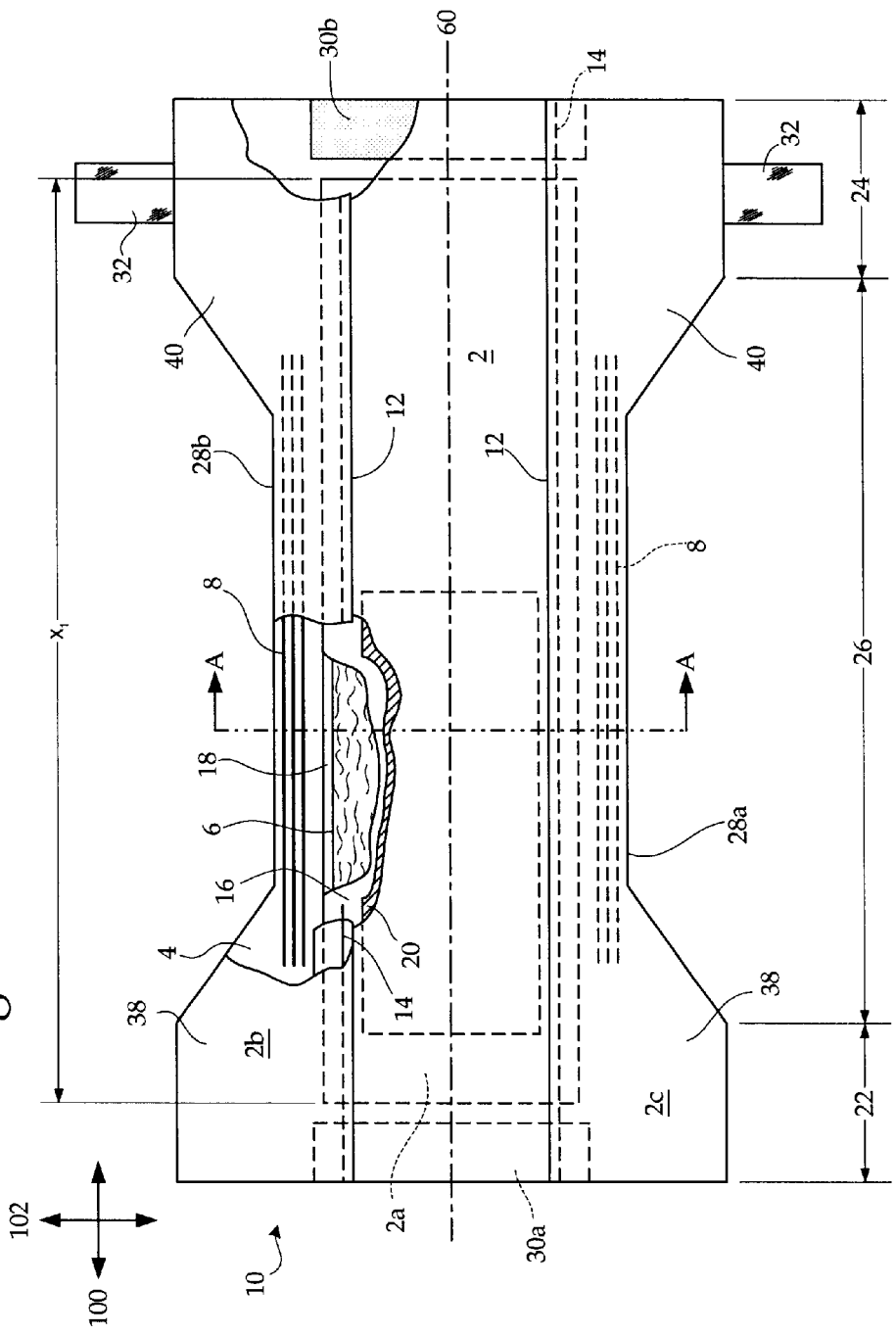
FIG. 1 is a plan view of a diaper-type absorbent garment, shown with the effects of elastics removed for clarity.

As used herein, the term "absorbent garment" or "garment" refers to garments that absorb and contain exudates, and more specifically, refers to garments that are placed against or in proximity to the body of the wearer to absorb and contain the various exudates discharged from the body. A non-exhaustive list of examples of absorbent garments includes diapers, diaper covers, disposable diapers, training pants, feminine hygiene products and adult incontinence products. The term garment includes all variations of absorbent garments, including disposable absorbent garments that are intended to be discarded or partially discarded after a single use (i.e., they are not intended to be laundered or otherwise restored or reused) and unitary disposable absorbent garments that have essentially a single structure (i.e., do not require separate manipulative parts such as a diaper cover and insert). As used herein, the term "diaper" refers to an absorbent garment generally worn by infants and incontinent persons about the lower torso.

The claims are intended to cover all of the foregoing classes of absorbent garments, without limitation, whether disposable, unitary or otherwise. These classifications are used interchangeably throughout the specification, but are not intended to limit the claimed invention. The invention will be understood to encompass, without limitation, all classes of absorbent garments, including those described above. Preferably, the absorbent core is thin in order to improve the comfort and appearance of a garment. The importance of thin, comfortable garments is disclosed, for example, in U.S. Pat. No. 5,098,423 to Pieniak et al., which is incorporated herein by reference in its entirety and in a manner consistent with the present invention.

Absorbent garments and diapers may have a number of different constructions. In each of these constructions it is generally the case that an absorbent core is disposed between a liquid pervious, body-facing topsheet, and a liquid impervious, exterior facing backsheet. In some cases, one or both of the topsheet and backsheet may be shaped to form a pant-like garment. In other cases, the topsheet, backsheet and absorbent core may be formed as a discrete assembly that is placed on a main chassis layer and the chassis layer is shaped to form a pant-like garment. The garment may be provided to the consumer in the fully assembled pant-like shape, or may be partially pant-like and require the consumer to take the final steps necessary to form the final pant-like shape. In the case of training pant-type garments and most adult incontinent products, the garment is provided fully formed with factory-made side seams and the garment is donned by pulling it up the wearer's legs. In the case of diapers, a caregiver usually wraps the diaper around the wearer's waist and joins the side seams manually by attaching one or more adhesive or mechanical tabs, thereby forming a pant-like structure. For clarity, the present invention is described herein only with reference to a diaper-type garment in which the topsheet, backsheet and absorbent core are assembled into a structure that forms a pant-like garment when secured on a wearer using fastening devices, although the invention may be used with other constructions.

Throughout this description, the expressions "upper layer," "lower layer," "above" and "below," which refer to the various components included in the absorbent garments of the invention (including the layers surrounding the absorbent core units), as well as the depiction in the drawings of certain layers or materials that are "above" or "below" one another, are used merely to describe the spatial relationship between the respective components. The upper layer or component "above" the other component need not always remain vertically above the core or component, and the lower layer or component "below" the other component need not always remain vertically below the core or component. Indeed, embodiments of the invention include various configurations whereby the core may be folded in such a manner that the upper layer ultimately becomes the vertically highest and vertically lowest layer at the same time. Other configurations are contemplated within the context of the present invention.

The term "component" can refer, but is not limited, to designated selected regions, such as edges, corners, sides or the like; structural members, such as elastic strips, absorbent pads, stretchable layers or panels, layers of material, or the like; or a graphic.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

Throughout this description, the expression "fibrous material" denotes any fibrous material that may be used in an absorbent garment, including without limitation, various hardwood and softwood fluff pulps, tissues, cottons, and any other fibrous materials described herein. "Fibrous material" used in the context of the present invention is not intended to limit the invention to any particular type of fibrous material.

Throughout this description, the expression "tow fibers" relates in general to any continuous fiber. Tow fibers typically are used in the manufacture of staple fibers, and preferably are comprised of synthetic thermoplastic polymers. Usually, numerous filaments are produced by melt extrusion of the molten polymer through a multi-orifice spinneret during manufacture of staple fibers from synthetic thermoplastic polymers in order that reasonably high productivity may be achieved. The groups of filaments from a plurality of spinnerets typically are combined into a tow which is then subjected to a drawing operation to impart the desired physical properties to the filaments comprising the tow.

A preferred embodiment of the present invention comprises a disposable absorbent garment 10 of the diaper type, such as shown, for example, in FIG. 1. It should be understood, however, that the present invention is applicable to other types of absorbent garments. With reference to FIG. 1, the diaper 10 according to a first preferred embodiment is shown in a relaxed condition with the effects of the elastics removed for purposes of clarity in the description. The diaper 10 has a generally hourglass shape and can generally be defined in terms of a front waist region 22, a back waist region 24, and a crotch region 26. Those skilled in the art will recognize that "front" and "back" are relative terms, and these regions may be transposed without departing from the scope of the present invention. Alternatively, the diaper can be configured in a generally rectangular shape or in a "T" shape. A pair of leg openings 28a, 28b extend along at least a portion of the crotch region 26. The diaper preferably comprises a topsheet 2, a backsheet 4, which may be substantially coterminous with the topsheet 2, and an absorbent core 6 disposed between at least a portion of the topsheet 2 and backsheet 4. One or more pairs of leg elastics 8 (three pairs are shown in FIG. 1) may be disposed to extend adjacent to leg openings 28a, 28b, respectively. Of course, in other embodiments, the leg elastics 8 may be omitted altogether.

The diaper may further include a front waist elastic system 30a, a back waist elastic system 30b, a fastening system 32 (e.g., tape or other suitable mechanical fastener) and a waste containment system in the form of waste containment flaps 12 (also known as standing leg gathers). Waste containment flaps 12 (FIG. 2) preferably extend from the front waist region 22 to the back waist region 24 along opposite sides of a longitudinal center line or axial center line 60 of the diaper 10, or alternatively only along a portion thereof. The front waist region 22 and rear waist region 24 may include ear portions 38, 40 extending outwardly from the leg openings 28a, 28b.

A variety of backsheet and topsheet constructions and materials are available and known in the art, and the invention is not intended to be limited to any specific materials or constructions of these components. The backsheet 4 is of any suitable pliable liquid-impervious material known in the art. Typical backsheet materials include films of polyethylene, polypropylene, polyester, nylon, and polyvinyl chloride and blends of these materials. For example, the backsheet can be a pigmented polyethylene film having a thickness in the range of 0.02–0.04 mm. The moisture-pervious topsheet 2 can be any suitable relatively liquid-pervious material known in the art that permits passage of liquid therethrough. Non-woven topsheet materials are exemplary because such materials readily allow the passage of liquids to the underlying absorbent core 6. Examples of suitable topsheet materials include non-woven spunbond or carded webs of polypropylene, polyethylene, nylon, polyester and blends of these materials.

The backsheet 4 and the topsheet 2 preferably are "associated" with one another. The term "associated" encompasses configurations whereby the topsheet 2 is directly joined to the backsheet 4 by affixing the topsheet 2 directly to the backsheet 4, and configurations whereby the topsheet 2 is indirectly joined to the backsheet 4 by affixing the topsheet 2 to intermediate members which in turn are affixed to the backsheet 4. While the backsheet 4 and topsheet 2 in the preferred embodiment have substantially the same dimensions, they may also have different dimensions.

In addition, the backsheet 4 may be covered with a fibrous, nonwoven fabric such as is disclosed for example in U.S. Pat. No. 4,646,362, which is incorporated herein by reference in its entirety and in a manner consistent with the present invention. Materials for such a fibrous outer liner include a spun-bonded nonwoven web of synthetic fibers such as polypropylene, polyethylene or polyester fibers; a nonwoven web of cellulostic fibers, textile fibers such as rayon fibers, cotton and the like, or a blend of cellulostic and textile fibers; a spun-bonded nonwoven web of synthetic fibers such as polypropylene; polyethylene or polyester fibers mixed with cellulostic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulostic, pulp or textile fibers.

The backsheet 4 may comprise multiple panels, such as three panels wherein a central poly backsheet panel is positioned adjacent the absorbent core while outboard nonwoven breathable side backsheet panels are attached to the side edges of the central poly backsheet panel. The backsheet may also be formed from microporous poly coverstock for added breathability. In other embodiments, the backsheet may be a laminate of several sheets. The backsheet may further be treated to render it hydrophilic or hydrophobic, and may have one or more visual indicators associated with it, such as labels indicating the front or back of the diaper or other characters or colorations. The present invention is not limited to any particular backsheet 4 material or construction.

The topsheet 2 may be formed from one or more panels of material and may comprise a laminated sheet construction. In the embodiment of FIG. 1, the topsheet comprises three separate portions or panels. A three-panel topsheet may comprise a central topsheet panel 2a (FIG. 2) that preferably is formed from a liquid-pervious material that is either hydrophobic or hydrophilic. The central topsheet panel 2a may be made from any number of materials, including synthetic fibers (e.g., polypropylene or polyester fibers), natural fibers (e.g., wood or cellulose), apertured plastic films, reticulated foams and porous foams to name a few. One preferred material for a central topsheet panel 2a is a cover stock of single ply non-woven material which may be made of carded fibers, either adhesively or thermally bonded, perforated plastic film, spunbonded fibers, or water entangled fibers, which generally weigh from 0.3–0.7 oz./yd$^2$ and have appropriate and effective machine direction and cross-machine direction strength suitable for use as a baby diaper cover stock material, as are known in the art. The central topsheet panel 2a preferably extends from substantially the front waist region 22 to the back waist region 24 or a portion thereof.

The second and third topsheet panels 2b, 2c in this embodiment may be positioned laterally outside of the central topsheet panel 2a. The outer topsheet panels 2b, 2c preferably are substantially liquid-impervious and hydrophobic, preferably at least in the crotch area. The outer edges of the outer topsheet panels may substantially follow the corresponding outer perimeter of the backsheet 4. The material for the outer topsheet portions or panels preferably is polypropylene and can be woven, non-woven, spunbonded, carded or the like, depending on the application.

An inner region 34 (FIG. 2) of the outer topsheet portions or panels 2b, 2c preferably is attached by, e.g., an adhesive, to the outer edges 36 of the inner topsheet portion or panel 2a. At the point of connection with the outer edges 36 of the inner topsheet portion or panel 2a, the inner regions 34 of the outer topsheet portions or panels 2b, 2c extend upwardly to form waste containment flaps 12. The waste containment flaps 12 may be formed of the same material as the outer topsheet portions or panels 2b, 2c, as in the embodiment shown. The waste containment flaps 12 may also be formed from separate elasticized strips of material that are associated with the topsheet, backsheet or both, or otherwise integrated into the garment.

The waste containment flaps 12 may be treated with a suitable surfactant to modify their hydrophobicity/hydrophilicity or imbue them with skin wellness products as desired. The central topsheet portion or panel 2a may extend past the connection point with the waste containment flaps 12 and even extend to the periphery of the backsheet. Still further, the central topsheet portion or panel 2a could extend fully between the outer topsheet portions or panels 2b, 2c and even beyond so that the outer edges 36 of the central topsheet portion or panel 2a are coextensive with and sandwiched between the outer topsheet portions or panels 2b, 2c and the backsheet 4.

The waste containment flaps 12 each preferably includes a portion that folds over onto itself to form an enclosure. One or more elastic members 14 (FIG. 2) may be secured in the enclosure in a stretched condition. As has been known at least as long the disclosure of Tetsujiro, Japanese Patent document 40-11543, when the flap elastic 14 attempts to assume the relaxed, unstretched condition, the waste containment flaps 12 rise above the surface of the central topsheet portion or panel 2a. Various other configurations of topsheets 2 and waste containment systems, such as flaps 12, are known in the art, and the present invention is not intended to be limited to any particular design for these components.

The waist elastics 30a, 30b (FIG. 1) may be similar structures or different to impart similar or different elastic characteristics to the front and back waist portions 22, 24 of the diaper. In general, the waist elastics may comprise elastically extensible foam strips positioned at the front and back waist sections 22, 24. The foam strips are preferably about 0.50 inches to about 1.50 inches wide and about 3 inches to about 6 inches long. The foam strips are preferably positioned between the topsheet portions or panels and the backsheet 4. Alternatively, a plurality of elastic strands may be employed as waist elastics rather than foam strips. The foam strips are preferably polyurethane, but could be any other suitable material that preferably decreases waist band roll over, reduces leakage over the waist ends of the absorbent garment, and generally improves comfort and fit. The front and back waist foam strips 30a, 30b are stretched 50–150%, preferably 100% before being adhesively secured between the backsheet 4 and topsheet 2. Waist elastics are known in the art, and the present invention is not limited to the use of a particular waist elastic system, or to the inclusion of waist elastics at all.

Each leg opening 28a, 28b may be provided with a leg elastic containment system 8, sometimes referred to as conventional leg gathers. In a preferred embodiment, three strands of elastic threads are positioned to extend adjacent the leg openings 28a, 28b between the outer topsheet portions or panels 2b, 2c and the backsheet 4. the selection of appropriate elastics and the construction of leg elastic containment systems is known in the art. For example, the leg elastics 8 may be ultrasonically bonded, heat/pressure sealed using a variety of bonding patterns, or glued to the diaper 10.

Various commercially available materials may be used for the leg elastics 8 and elastic members 14, such as natural rubber, butyl rubber or other synthetic rubber, urethane, elastomeric materials such as spandex, which is marketed under various names, including LYCRA (DuPont), GLOSPAN (Globe) and SYSTEM 7000 (Fulflex), and so on. The present invention is not limited to any particular elastic.

The fastening system of the diaper 10 may be attached to the back waist region 24, and preferably comprises tape tabs or mechanical fasteners 32. However, any fastening known in the art will be acceptable. Moreover, the fastening system may include a reinforcement patch below the front waist portion so that the diaper may be checked for soiling without compromising the ability to reuse the fastener. Alternatively, other diaper fastening systems are also possible, including safety pins, buttons, and snaps. Fastening systems are known in the art, and the present invention is not limited to using any particular fastening, and may be constructed without any fastening system at all, such as in training pant-type garments.

As stated previously, the invention has been described in connection with a diaper. The invention, however, is not intended to be limited to application only in diapers. Specifically, the present invention may be readily adapted for use in other absorbent garments besides diapers, including, but not limited to, training pants, feminine hygiene products and adult incontinence products.

Figure 2:
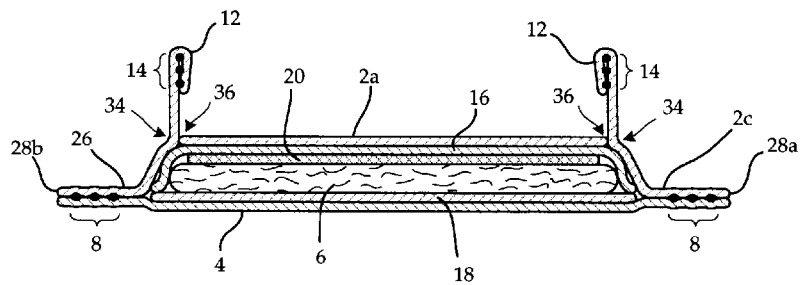
FIG. 2 is a cross-sectional view of the garment of FIG. 1, as viewed from reference line AA.

The underlying structure beneath the topsheet 2 may include, depending on the diaper construction, various combinations of elements, but in each embodiment, it is contemplated that the absorbent garment will preferably include an absorbent core 6. For example, an additional layer 20 may be disposed between the topsheet 2 and absorbent core 6, as shown in FIG. 2, and/or other additional layers may be disposed between these layers, or between absorbent core 6 and backsheet 4. The additional layer 20 or layers may comprise any useful layer known in the art or developed hereafter, such as a fluid acquisition layer, a distribution layer, an additional fibrous layer optionally containing SAP, a wicking layer, a storage layer, or combinations and fragments of these layers. Such layers may be provided to assist with transferring fluids to the absorbent core 6, handling fluid surges, preventing rewet, containing absorbent material, improving core stability, or for other purposes. Skilled artisans are familiar with the various additional layers that may be included in absorbent article, and the present invention is not intended to be limited to any particular type of materials used for those layers. Rather, the invention encompasses all types of wicking layers, all types of distribution layers, etc., to the extent that type of layer 20 is utilized.

The dimensions of additional layer(s) 20 may be the same as or different from the dimensions of the absorbent core 6 and/or topsheet 2 and backsheet 4. It is preferred that additional layer(s) 20 have a width in the lateral direction (102) of anywhere from about 10 mm to about 100 mm, and preferably from about 25 mm to about 80 mm.

Although the absorbent core 6 depicted in FIG. 1 has a substantially rectangular shape as viewed in the plan view, other shapes may be used, such as a "T" shape or an hourglass shape. The absorbent core 6 may extend into either or both of the front and back waist regions 24, 22. The shape and construction of the absorbent core 6 may be selected to provide the greatest absorbency in target areas where body fluids are most likely to strike the diaper 10, which is often referred to as zoned absorbency. The absorbent core 6 may also comprise a number of layers of similar or different construction. The absorbent core may be associated with the topsheet 2, backsheet 4, or any other suitable part of the garment 10 by any method known in the art, in order to fix the absorbent core 6 in place.

Generally, in a preferred embodiment, the absorbent core 6 comprises particles of super absorbent polymer distributed within a fibrous structure. Additional fibrous or particulate additives may be disposed within the absorbent core 6 to add to the core's strength and SAP efficiency or to otherwise enhance the performance of the garment. The absorbent core 6 may be partially or wholly surrounded by a tissue layer 16, 18, and other additional layers 20 may be added to provide further benefits. The various components of the absorbent core 6 are now described in greater detail.

Certain fibrous materials preferably are used to form the fibrous structure of the absorbent core 6 of the present invention. These fibrous materials maintain high SAP efficiencies when the SAP concentration is in the range of about 50–95%, more preferably about 60–90%, and most preferably about 75–85%. For example, the fibrous structure of the absorbent core 6 may be made with cellulose acetate fibers, rayon fibers, Courtauld's LYOCELL fibers, polyacrylonitrile fibers, surface-modified (hydrophilic) polyester fibers, surface-modified polyolefin/polyester bicomponent fibers, surface-modified polyester/polyester bicomponent fibers, cotton fibers, blends of the foregoing materials, and the like.

Of the foregoing, cellulose acetate tow fibers are the most preferred materials for use as the fibrous structure. In addition, rayon, Courtauld's LYOCELL, polyacrylonitrile, cotton fibers and cotton linters have similar properties to cellulose acetate and are alternatively preferred. The remaining fibers, surface-modified polyolefin/polyester bicomponent fibers, and surface-modified polyester/polyester bicomponent fibers are also believed to be effective as a fibrous structure or as fibrous additives. To maintain high SAP concentrations, the weight concentration of fibrous material forming the absorbent core 6 of the invention preferably is about 5–50%, more preferably about 10–30%, and most preferably about 15–25%. Most preferably, the absorbent core 6 comprises from about 75–85% SAP and from about 15–25% fibrous structure material chosen from the foregoing group.

In accordance with the present invention, improved absorbent articles are advantageously based upon continuous crimped filament tow, and accordingly, the central fibrous structure of the core 6 is advantageously prepared therefrom. This fiber structure has high structural integrity, and as such, is distinct from a matrix of discontinuous fibers, often described as fluff or fluff pulp, that is commonly used in the prior art. The high structural integrity enables the production of stronger webs than those formed from discontinuous fibers, which in turn are believed to enable the production of thinner absorbent pads. In addition, the use of such fibers enables the production of ultra low density absorbent cores, when compared to absorbent cores prepared by dispersing SAP particles in fluff. The reduction in density is largely attributable to the reduced weight of the fibrous structure. Absorbent cores 6 constructed from a blend of such materials and SAP are referred to herein as "tow/SAP" cores or "tow-based" cores.

Beneficially, cellulose ester tow is used to form the fibrous structure. Non-limiting examples of suitable cellulose esters include cellulose acetate, cellulose propionate, cellulose butyrate, cellulose caproate, cellulose caprylate, cellulose stearate, highly acetylated derivatives thereof such as cellulose diacetate, cellulose triacetate and cellulose tricaproate, and mixtures thereof such as cellulose acetate butyrate. A suitable cellulose ester will include the ability to absorb moisture, preferably is biodegradable, and is influenced not only by the substituent groups but also by the degree of substitution. The relationship between substituent groups, degree of substitution and biodegradability is discussed in W. G. Glasser et al, BIOTECHNOLOGY PROGRESS, vol. 10, pp. 214–219 (1994), the disclosure of which is incorporated herein by reference in its entirety.

Continuous filament tow useful in the present invention is beneficially moisture-absorbent and biodegradable.

Accordingly, cellulose acetate tow typically is preferred for use in the invention. Typically, the denier per fiber (dpf) of the tow fiber will be in the range of about 1 to 9, preferably about 3 to 6, and most preferably about 4. For the same weight product, filaments of lower dpf may provide increased surface area and increased moisture absorption. Total denier of the tow may vary within the range of about 20,000 to 60,000, depending upon the process used, and is preferably about 35,000. The fibers may have a circular, ovate, rectilinear, or any other cross section. In one embodiment, the fibers have a tri-lobal cross section with an area of about $3.36 \times 10^{-6}$ cm$^2$. Such a cross-sectional shape may provide improved bending stiffness, increased wicking, or other beneficial properties.

Tow typically is provided as a relatively dense matrix of fibers, and it is often desirable to "open" (also known as "fluffing" or "blooming") the tow into a more voluminous cotton-like matrix. To this end, it is particularly preferred in the invention to use tow having crimped filaments, as the crimps aid with opening the tow. The separation of filaments resulting from the opening process advantageously results in increased available filament surface area for superabsorbent material immobilization and increased moisture absorption. Gel blocking also may be reduced by using crimped tow in the absorbent core 6. As therefore may be understood, more crimp is typically better, with an excess of about 20 crimps per inch being usually preferred. Continuous filament cellulose ester tow having crimped filaments with about 25 to 40 crimps per inch is commercially available from Hoechst Celanese Corporation of Charlotte, N.C.

If desired, an absorbent core 6 of multiple layer thickness may be provided. To this end, the tow may be, for example, lapped or crosslapped in accordance with conventional procedures. In this way, a superabsorbent, absorptive material of a desired weight and/or thickness may be provided. The specific weight or thickness will depend upon factors including the particular end use.

Any superabsorbent polymer (SAP) now known or later discovered may be used in the absorbent core 6, so long as it is capable of absorbing liquids. Useful SAP materials are those that generally are water-insoluble but water-swellable polymeric substances capable of absorbing water in an amount that is at least ten times the weight of the substance in its dry form. In one type of SAP, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Also included are water swellable polymers of water soluble acrylic or vinyl monomers crosslinked with a polyfunctional reactant. Such modified polymers may also be cross-linked to reduce their water-solubility, and such cross-linked SAPs have been found to provide superior performance in some absorbent cores. A more detailed recitation of superabsorbent polymers is found in U.S. Pat. No. 4,990,541 to Nielsen, the disclosure of which is incorporated herein by reference in its entirety. The SAP is preferable selected to provide high absorbency performance for the particular application. The measure of the SAP's absorbency performance may be evaluated in a number of ways, as will be understood by those skilled in the art. For example, it may be desirable to provide a SAP having a high measure of saline flow conductivity (SFC), as is described in U.S. Pat. No. 5,562,646 to Goldman et. al, which is incorporated herein by reference in its entirety and in a manner consistent with the present invention. Of course, the SAP may be selected to provide other properties or combinations of properties as well.

Commercially available SAPs include a starch modified superabsorbent polymer available under the trade name SANWET® from Hoechst Celanese Corporation, Portsmouth, Va. SANWET® is a starch grafted polyacrylate sodium salt. Other commercially available SAPs include a superabsorbent derived from polypropenoic acid, available under the trade name DRYTECH® 520 SUPERABSORBENT POLYMER from The Dow Chemical Company, Midland Mich.; AQUA KEEP manufactured by Seitetsu Kagaku Co., Ltd.; ARASORB manufactured by Arakawa Chemical (U.S.A.) Inc.; ARIDALL 1125 manufactured by Chemdall Corporation; and FAVOR manufactured by Stockhausen Inc. Still other commercially available SAPs include SA55SX, avalable from Sumitomo Chemical Co. Ltd. of Osaka, Japan, and T7700 and T7200 provided by BASF of Mount Olive, N.J.

The SAP may be provided in any particle size, and suitable particle sizes vary greatly depending on the ultimate properties desired. Preferably, a fine particulate rather than a coarse particulate, is used in the invention, and preferably a fine particulate that passes through an about 200 mesh screen is used.

It has been known to prepare absorbent cores comprised of cellulose acetate tow or other polymeric fibers and SAP, as described in U.S. Statutory Invention Registration H1565, and U.S. Pat. Nos. 5,436,066, and 5,350,370, the disclosures of each of which are incorporated by reference herein in their entirety and in a manner consistent with the present invention. It was conventional to add tackifying agents, specific size fibers, or specific fibers in combination with fluff, in order to prepare the absorbent core and immobilize the SAP particles. These additional materials may add to density of the core, or otherwise adversely affect the overall performance of the absorbent garment made therefrom. Thus, it is preferred not to use ethylene glycol, tackifying agents, and very small particulate fibers in the invention, although they may be used to the extent they do not reduce the overall performance of the garment.

The total basis weights of the absorbent core 6 including fibrous materials, SAP, tissue, additional layers, and additives, are anywhere from about 100 grams per square meter (gsm) to about 1,000 gsm. The most preferred total basis weights of the absorbent core 6 are about 500 gsm to about 700 gsm.

Additional particles or fibrous additives may be added to the absorbent core 6 to help maintain high SAP efficiency, to reduce the cost of the garment, or to provide other benefits. Fibrous additives may be introduced as part of the supply of unopened fibers, preferably tow fibers, or may be added to the fibers, preferably tow fibers, after it has been opened. In a preferred embodiment, particulate additives generally may be added to the tow after it has been opened to allow practical manufacture of the tow and to prevent losses of the particulate additives during processing.

In one embodiment, about 1–10%, and preferably about 5%, by weight of thermally bondable synthetic fibers may be added to the absorbent core 6 to impart additional wet strength to the laminate. These additive fibers may improve the stability of the core during use of the diaper. The preferred synthetic fibers for such an embodiment are polyolefin/polyester fibers and polyester/polyester bicomponent fibers.

In another embodiment, the fibrous structure may comprise a combination of preferred tow materials, such as a blend of cellulose ester and conventional soft or hard wood fibers. Such combinations may be useful to maintain the improved SAP efficiency available from the crimped filament tow-based fibrous structure while providing additional benefits. For example, it has been discovered that an absorbent core 6 having a 150 g/m$^2$ composite comprised of 80% SAP, 10% cellulose acetate, and 10% conventional fluff pulp has a SAP efficiency of about 85%, whereas an absorbent core 6 comprised of 80% SAP and 20% fluff pulp SAP has an efficiency of about 70%.

The particulate additives that may be added to the absorbent core 6 preferably are insoluble, hydrophilic polymers with particle diameters of 100 μm or less. These particulate additives may be chosen to impart optimal separation of the SAP particles. Examples of preferred particulate additive materials include, but are not limited to, potato, corn, wheat, and rice starches. Partially cooked or chemically modified (i.e., modifying hydrophobicity, hydrophilicity, softness, and hardness) starches can also be effective. Most preferably, the particulate additives comprise partially cooked corn or wheat starch because in this state, the corn or wheat are rendered larger than uncooked starch and even in the cooked state remain harder than even swollen SAP. In any event, regardless of the particulate additive chosen, one of the many important criteria is to use particulate additives that are hard hydrophilic materials relative to swollen SAP or which are organic or inorganic polymeric materials about 100 microns in diameter. Fibrous and particulate additives can be used together in these absorbent laminates. Examples of SAP/particulate and SAP/fiber/particulate additives include those described in, for example, U.S. Pat. No. 6,068,620.

Other particulate or powdered additives also may be deposited within the absorbent core 6 to provide odor control, skin wellness, and improved appearance. For example, zeolites, sodium bicarbonate and perfumes may be added to reduce or mask odors, and titanium dioxide or other color-imbuing compounds may be added to provide the absorbent core 6 with a more pleasant color.

The absorbent core 6 preferably comprises a tissue wrapping that at least partially encloses the preferred blended tow and SAP, such as disclosed in U.S. Pat. No. 6,068,620. The tissue wrapping is useful, for example, for containing the SAP within the absorbent core 6 and providing strength to the core during manufacturing and use. In a preferred embodiment, the tissue wrapping comprises first and second tissue layers 16, 18 that encase the absorbent core 6, and may optionally also encase one or more additional layers 20. Preferably, the first tissue layer 16 is located generally between the topsheet 2 and the absorbent core 6, and is hydrophilic and fluid pervious. It is also preferred that the second tissue layer 18 be located between the backsheet 4 and the absorbent core 6 and be hydrophobic and fluid impervious. The tissue wrapping may also comprise a single tissue layer that has been folded to encase the absorbent core, and that may be zone treated to render the portion that forms the lower tissue layer 18 hydrophobic and fluid impervious. The tissue layers 16, 18 or the whole core 6 may be crimped, folded, sealed or bonded to help contain the SAP particles.

In one embodiment, the fibrous structure and SAP of the absorbent core may be adhesively or thermally bonded to improve the absorbent core's wet strength and core stability. This, unfortunately, may result in slower than adequate rates of absorption and poor SAP efficiency. In another embodiment the SAP and fibrous structure may be hydrogen bonded to additional the tissue layers 16, 18. When a tow-based fibrous structure having a high concentration of SAP is hydrogen bonded to first and second tissue layers 16, 18 to form an absorbent core 6, the SAP efficiency is not impaired, wet strength increases, and the first and second tissue layers 16, 18 add stability to the core 6 during manufacture. It has been found that when the fibrous structure of the absorbent core 6 is hydrogen bonded using water to the tissue layers 16, 18, unexpectedly good "core utilization" is realized. "Core utilization" is the percentage of the total capacity of a core that can be absorbed in a demand absorbency test. This unexpected performance improvement is believed to be the result of the beneficial liquid distribution provided by the intimate bond between the fibers of the fibrous structure and the tissue layers 16, 18.

In another preferred embodiment, the first and second tissue layers 16, 18 are coated with adhesive prior to being placed on either side of the absorbent core 6, thereby providing strength to the core and adhesively holding a portion of the SAP in place during use. The tissue layers 16, 18 may be provided having a width greater than the fibrous structure of the absorbent core 6, and the portions of the tissue layers 16, 18 extending past either side of the fibrous structure of the core 6 may be bonded to one another to provide further SAP retention capability. In still another embodiment, if the fibrous structure contains about 1–5% by weight thermally bondable synthetic fibers, bonding to the tissue layers 16, 18 may be achieved using thermal bonds.

The absorbent core 6 of the present invention may flat or folded when it is fixed in place between the topsheet 2 and backsheet 4. Folded cores may provide additional performance benefits, such as improved fluid redistribution, greater SAP efficiency, and so on. The absorbent core 6 can be folded in any suitable manner, including any and all of those disclosed in U.S. Pat. No. 6,068,620. Those skilled in the art will appreciate that the absorbent core 6 can be folded such that the adjacent sides are touching one another, or so that channels are formed in certain areas. For example, the absorbent core 6 can be folded in the form of a "C" where the curled ends may be spaced apart to form a channel there between, and the lower edges of the curled ends may be disposed adjacent the upper edges of the bottom portion of the folded article. Alternatively, another absorbent material, or another absorbent core 6 may be disposed in the space formed by the standard "C" fold. The same considerations may be given to embodiments having a "G" fold or a "U" fold where the spaces formed by these folds may be filled with another absorbent material, another absorbent core 6, left open to form fluid handling channels, or the folds may be made tight enough so that little or no space is formed. Other possible arrangements include a "Z" fold, and a pleated absorbent core 6, and other folded shapes, as will be appreciated by those skilled in the art.

The absorbent core 6 preferably is formed using a dry process. Dry processes have numerous benefits over wet processes. For example, in wet processes, the core material is typically immersed in a fluid having a superabsorbent particles mixed or suspended therein, and the core material may require additional drying steps and other steps that add to the complexity and cost of the core forming process. In addition, wet processes often require the absorbent core to be manufactured off of the main assembly line. Dry processes typically have lower operating costs than wet processes because the equipment used in dry processes is typically less complex and can run at higher line speeds. Further, dry forming processes may often be adapted for use directly on the line of conventional diaper machines. A preferred embodiment of the present invention is particularly concerned with using a dry forming process to manufacture absorbent cores having high concentrations of SAP and relatively low basis weights, while overcoming or avoiding the deficiencies of known dry forming processes and machines, as described elsewhere herein.

One challenge with making absorbent cores having high concentrations of SAP and relatively low basis weight fibrous structures, as described above, is to achieve the desired distribution of SAP within the core. In many cases it may be desirable to achieve a uniform distribution of SAP within the core to provide the absorbent garment with uniform absorption capability. In such a case, not only should the SAP be evenly distributed along the length and width of the absorbent core, but it also should be properly distributed throughout the thickness of the core to ensure that the SAP is not subject to gel blocking or other inefficiencies during use. It also is desirable to provide a controlled amount of SAP to the core to prevent overuse of the SAP, which typically is relatively expensive. It may be further desirable to precisely control the distribution of SAP to provide local regions of the core that have greater SAP concentrations than others to provide zoned absorbency. Such concentrations may be along one or more of the absorbent core's length, width and thickness.

Figure 3:
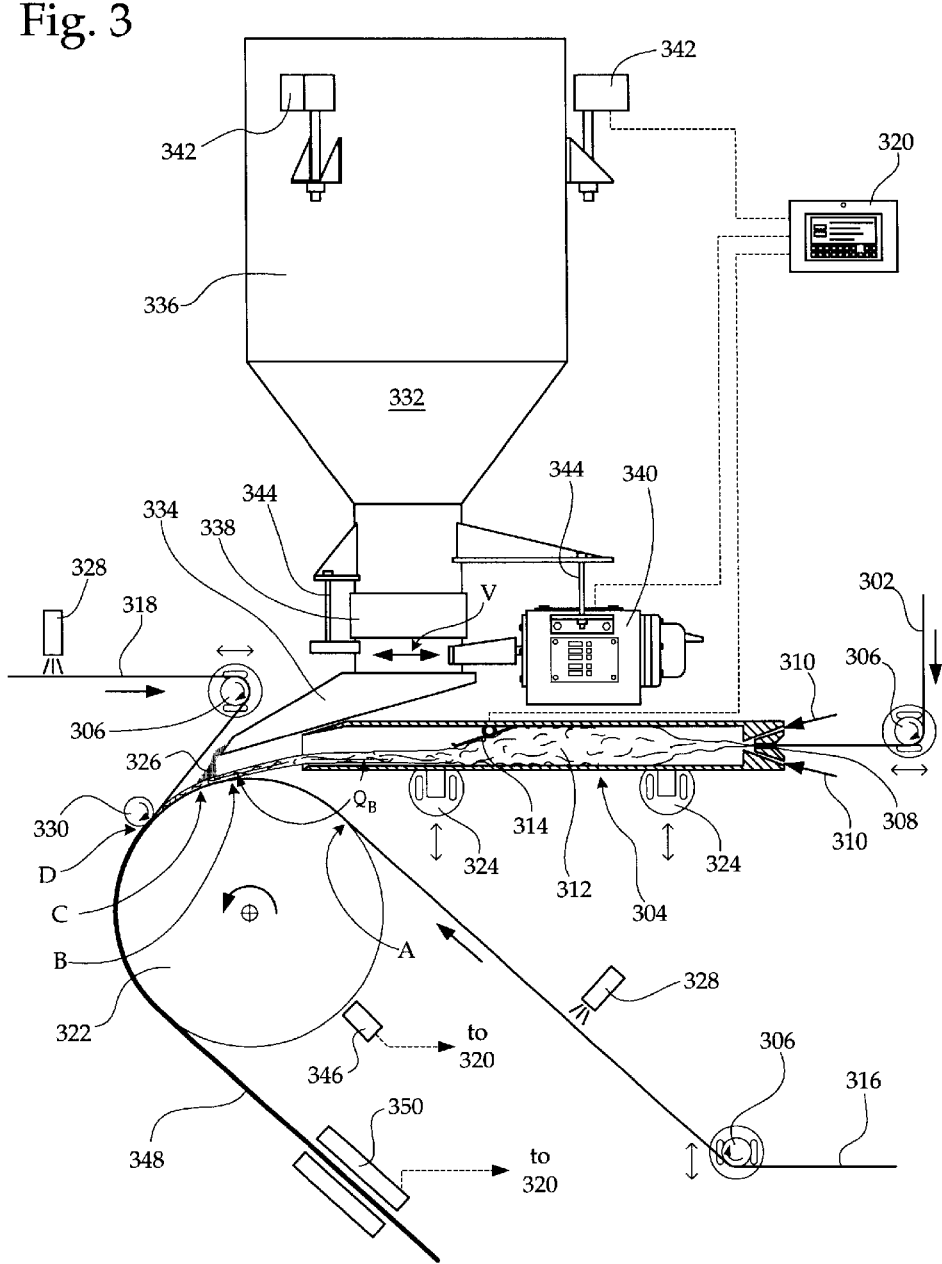
FIG. 3 is a partially cut away schematic elevational view of a system for dry forming absorbent cores and other structures and machinery according to a preferred embodiment of the present invention, shown in operation and in relation to a portion of an absorbent garment manufacturing line.

Referring now to FIG. 3, a preferred embodiment of an apparatus and method for dry forming composite cores is shown. In the preferred embodiment, a tow supply 302, which may be unopened or partially opened, is provided along a first path to enter a forming jet assembly 304. The supply of tow may comprise any material that is desired to be used as the fibrous structure of the garment's absorbent core 6 and is suitable for use in the process described herein, such as those that have been described elsewhere herein. Those skilled in the art will appreciate that if fibers, fluff, or pulp other than tow fibers are used, forming jet assembly 304 would be replaced by a suitable fiber or fluff forming apparatus, as are well known in the art. A preferred material for the tow supply 302 is a supply of cellulose acetate having a basis weight of about 50 g/m² to about 100 g/m², and more preferably of about 76 g/m². The tension, speed and path of the tow supply 302 may be adjusted by one or more movable pulleys 306, guides (not shown) and/or festoons (not shown), as are known in the art.

The tow supply 302 enters the forming jet assembly 304 and is opened in preparation for being incorporated into absorbent cores. The forming jet assembly 304 comprises a tow inlet 308 at one end into which the tow supply 302 is fed. One or more high velocity jets 310 of air or other gas are projected into the forming jet assembly to impinge upon the tow supply 302 to thereby separate the fibers and "bloom" or open the tow. Preferably, two jets 310 are used and each jet 310 is located proximal to the tow inlet 308 and on opposite sides of the tow supply 302. Each of the jets 310 preferably comprises a flow of air moving at about 17.5 cubic feet per minute through a slit-shaped port that has a length of about 3.94 inches and a width of about 0.003 inches. Similar devices for opening tow are known in the art, and disclosed, for example, in U.S. Pat. No. 5,331,976 to St. Pierre, which is incorporated herein by reference in its entirety and in a manner consistent with the present invention. Other devices and procedures for opening the tow supply 302 may also be used with the present invention, as will be understood by those skilled in the art.

The opened or "bloomed" tow 312 accumulates within the forming jet assembly 304 as it is being used, and the amount of opened tow 312 being consumed may be measured by a level meter 314 (also known as a "dancer"). The level meter 314 may be any suitable electromechanical, optical, or other type of device capable of measuring the amount of opened tow 312 being consumed. In a preferred embodiment, the level meter 314 is a plate that is pivotally attached to a rotary position sensor (such as a commonly known variable resistance or potential device). As the level of opened tow 312 increases or decreases, the plate pivots up and down, thereby changing the output of the rotary position sensor. In a preferred embodiment, the level meter 314 is used as part of a closed-loop feedback algorithm or an open-loop algorithm to meter the rate at which the tow supply 302 is fed into the forming jet assembly 304, and may be integrated into a control system 320.

The control system 320 may comprise any electrical control apparatus that may be configured to control one or more variables based on the measurement of one or more inputs. Although the control system 320 is referred to herein in the singular, it should be understood that a number of independent control systems 320 may be used for various parts of the machinery, and these various systems are referred to collectively herein as a single control system 320. The control system 320 may control any number of variables and have any number of inputs, and may use an open-loop or closed-loop algorithm. Exemplary control systems 320 include programmable logic control (PLC) devices having easily used human machine interfaces, as are known in the art. Of course, the control system 320 may simply comprise a human operator that monitors the various inputs and adjusts the various system variables.

Figure 8:
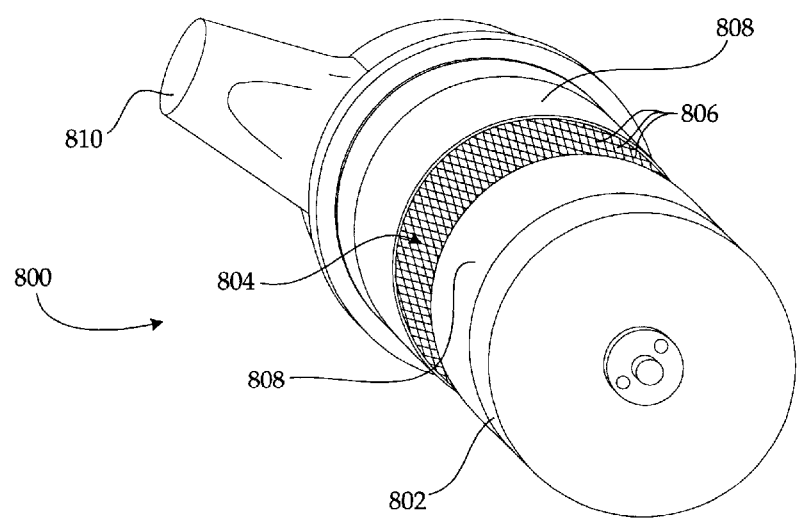
FIG. 8 is an isometric view of the outlet portion of a feed tray according to another embodiment of the present invention.

The opened tow 312 preferably is pulled out of the forming jet assembly 304 by a vacuum draw roll 322, such as the combining drum 800 described elsewhere herein in conjunction with FIG. 8, or a similar drawing device. The opened tow 312 exits the forming jet assembly 304 at a tow break angle $\Theta_B$, which may be adjusted by altering the position of the vacuum draw roll 322 (or similar device), or, more preferably, by adjusting the height and angle of the forming jet assembly 304 using adjustable mounts 324. Increasing the tow break angle $\Theta_B$ increases the drag on the opened tow 312 and thereby increases the amount of stretch that the vacuum draw roll 322 imparts on the opened tow 312. Greater stretch reduces the basis weight of the opened tow 312 that is pulled onto the vacuum draw roll 322. The tow forming jet 304 preferably is aligned so that its outlet is tangential to the vacuum draw roll 322 or slightly above a tangent to the vacuum draw roll 322. In a preferred embodiment, the outlet of the tow forming jet 304 is located at a tangent to the vacuum draw roll 322 to about 1 inch above a tangent to the vacuum draw roll 322. In a more preferred embodiment the outlet of the tow forming jet 304 is less than about 0.75 inches above a tangent to the vacuum draw roll 322, and in a most preferred embodiment, the outlet of the tow forming jet 304 is located less than about 0.5 inches above a tangent to the vacuum draw roll 322.

The tow forming jet's adjustable mounts 324 may be fixed in a desired position during machine operation, or may be actively operated by a control system 320 during operation in response to measurements of the core basis weight or other feedback gathered during operation. Mechanical, electromechanical, pneumatic, hydraulic, or other suitable adjusting devices may be used to actuate the adjustable mounts 324, such as stepper motors, solenoids and hydraulic or pneumatic pistons or rams, and the like. Alternatively, or in addition, the basis weight of the opened tow 312 may be adjusted by increasing or decreasing the speed of the vacuum draw roll 322, with faster speeds generally resulting in a lower basis weight of the opened tow 312.

After the opened tow 312 exits the forming jet assembly 304, a supply of superabsorbent particles 326 is delivered to the opened tow 312, and the tow/SAP composite is encased between first and second casing sheet supplies 316, 318. Alternatively, the tow/SAP composite may be encased within a fold in a single casing sheet. Preferably, as shown in FIG. 3, the opened tow 312 is laid onto a first casing sheet supply 316 before the SAP 326 is fed to the opened tow 312 to help contain the SAP 326 and control the SAP distribution, then the second casing sheet supply 318 is laid on the tow/SAP composite to form an absorbent core subassembly that may be processed into absorbent garments.

The first and second casing sheet supplies 316, 318 encase the opened tow and SAP composite. The first and second casing sheet supplies 316, 318 preferably form the first and second tissue layers 16, 18 of the completed garment, but may also form the topsheet 2 and backsheet 4 of the absorbent garment 10, or any other layers. The first and second casing sheet supplies 316, 318 are preferably wider than the opened tow 312 that forms the absorbent core 6, and their side portions are preferably sealed to one another by bonding or crimping to prevent release of opened tow 312 and particles of SAP. The absorbent core composite 348, comprising the assembly of the first and second casing sheet supplies 316, 318 and the opened tow 312 and SAP 326 core, may be further processed as it is conveyed through the assembly line for inclusion into absorbent garments 10. For example, in a preferred embodiment, the absorbent core composite 348 is severed into individual absorbent cores 6, and the severed ends may be crimped or bonded to prevent the SAP 326 from exiting the ends.

In all cases, at least one of the first and second casing sheets 316, 318 should be liquid permeable and positioned in the garment to face the wearer's body to allow the flow of fluids into the core 6. The other casing sheet supply may optionally be liquid impermeable. The liquid impermeability or permeability of either of the casing sheet supplies 316, 318 may be provided by chemical or physical treatment, or by the proper selection of materials, as is known in the art. In an alternative preferred embodiment, the first and second casing sheets 316, 318 may both be formed from a single sheet of material that is folded to encase the opened tow 312 and SAP 326.

It may be desirable to apply an adhesive to one or both of the first and second casing sheet supplies 316, 318 prior joining them with the opened tow 312 or tow/SAP combination. For example, in one preferred embodiment, an adhesive is applied to the entire width of one or both of the casing sheet supplies 316, 318 by adhesive applicators 328 before they are joined with the opened tow 312 to provide a better bond between the casing sheets 316, 318 and the tow/SAP composite. In such an embodiment, the adhesive may also function to fix a portion of the SAP particles 326 in place. In another preferred embodiment, the supplies casing sheet material 316, 318 are wider than the tow/SAP composite, and adhesive is applied along the lateral edges of one or both of the casing sheet supplies to join them to one another, thereby sealing in the tow/SAP composite. Other uses of adhesives will be apparent to those skilled in the art based on the teachings provided herein.

A preferred adhesive for these and other embodiments is H2561U hot melt construction adhesive, available from Atofindley of Wauwatosa, Wis. Other suitable adhesives, known in the art, may be used provided they do not excessively impair the desired properties of the casing sheet material (as described elsewhere herein), or add excessive stiffness to the absorbent core 6. For example, other adhesives may include HL-1258 by H. B. Fuller Company of St. Paul, Minn.; Findley 2031 and H2587-01 by Ato Findley Inc. of Wauwatosa, Wis.; and NS34-5665 by National Starch Co. of Bridgewater, N.J. Other adhesives that may be used include 34-578A by National Starch Co. of Bridgewater, N.J. In another preferred embodiment, the adhesive may be selected to impart desired properties to the casing sheet supplies 316, 318. For example, an adhesive may be used to render one of the casing sheet supplies 316, 318 fluid impervious, opaque, hydrophobic (or hydrophilic), and so on. the adhesive may also be water soluble or have other beneficial properties. Adhesive applicators that may be used with the present invention include spray applicators, such as those provided by Nordson Corporation of Westlake, Ohio, or other suitable applicators, as are known in the art.

Still referring to FIG. 3, in a preferred embodiment the absorbent core composite 348 is assembled in four procedures that take place as the various parts of the assembly are pulled onto the rotating vacuum draw roll 322. In the first step, which takes place at location A, the first casing sheet supply 316 is drawn onto the vacuum draw roll 322. In the second step, at location B, the opened tow 312 is drawn onto the vacuum draw roll 322 to overlay the first casing sheet supply 316 after being pulled out of the forming jet assembly 304. In the third step, at location C, a supply of SAP 326 is deposited onto the opened tow 312 by the vibratory feeder 332, as described herein. And in the fourth step, at location D, the second casing sheet supply 318 is brought in to overlie the first casing sheet supply 316, opened tow 312 and deposited SAP. Those skilled in the art will appreciate that these steps may be performed using equipment other than that specifically described herein, and may also be performed in various different orders, with some of the steps being rearranged, omitted or combined, or with additional steps being performed. Such variations are generally within the scope of the present invention.

Also in a preferred embodiment, a lay on roll 330 is used to press the second casing sheet supply 318 against the tow/SAP composite and the first casing sheet supply 316. The lay on roll 330 helps flatten the core assembly and improves the edge seals between the first and second casing sheet supplies 316, 318. The lay on roll 330 may also be equipped to provide ultrasonic, heat, or other bonds between one or more of the first and second casing sheets 316, 318 and the tow/SAP composite. In such an embodiment, the lay on roll 330 may cooperate with the vacuum draw roll 322 or other device to create the desired bonds. For example, portions of the lay on roll 330 may form ultrasonic horns, while corresponding portions of the vacuum draw roll 332 form ultrasonic anvils that, together, form an ultrasonic bond between the first and second casing sheet supplies 316, 318.

The superabsorbent particles preferably are provided by a vibratory feeder 332. The vibratory feeder 332 comprises a feed tray 334 or other feed unit that is attached to and driven by a vibrator 340. The vibrator 340 vibrates the feed tray 334, moving it back and forth in the direction of vibration V, as indicated by the double-headed arrow in FIG. 3. The feed tray 334 is supplied from above by a hopper 336 by way of a flexible coupling 338 that helps isolate the hopper 336 from the movement of the feed tray 334. The vibratory feeder is preferably suspended on one or more, and most preferably three, scales 342 that weigh the vibratory feeder 332 and its contents. The vibratory feeder 332 is preferably positioned so that none of its moving parts, particularly the vibrator 340 and feed tray 334 strike other parts of the machinery during operation.

Although a preferred embodiment of the feed tray 334 is illustrated herein, the feed tray 334 can include any of a variety of feed units adapted to convey particulate matter due to a vibration of the feed unit in accordance with the present invention. Examples of such vibratory feed units include trays, ramps, chutes, channels, troughs, tubes, gates, pans, boxes, drums, and the like, that are adapted to deposit particulate matter onto a target area when vibrated. These implementations of vibratory feed units, as well as other vibratory feed units known to those skilled in the art, can be implemented as the feed tray 334 without departing from the spirit or the scope of the present invention and the invention is not limited to any particular configuration or application of the feed tray. Rather, so long as the feeding unit or feeding tray supplies the SAP in accordance with the teachings herein, the specific construction of the feeding unit may vary from construction to construction and still be within the scope of the claimed invention.

The hopper 336 is preferably selected to provide consistent flow characteristics for a variety of superabsorbent polymers or other particulate and fibrous additives. In particular, it is preferred that the hopper 336 should flow all of its contents in a regular manner, described as "mass flow," so that few or none of the particles become stuck in the hopper 336, and do not experience sudden surges in the flow rate. Mass flow is present when essentially all of the material in the hopper is in motion whenever any material is withdrawn. This type of flow pattern is also described as first-in-first-out flow. In order to provide the desired mass flow, the hopper 336 is preferably designed to avoid "bridging" (i.e., when particles become lodged in the hopper by forming a "bridge" or arch-like structure that resists flowing), and to avoid "ratholing" (i.e., when a column of particles flows through the center of the hopper 336, but those particles along the walls do not flow). When the hopper 336 provides mass flow, it is not necessary to provide undesirable external forces, which may damage or redistribute the particles, to shake unmoving particles free. Mass flow may be obtained by providing the hopper 336 with relatively smooth interior walls and by avoiding the use of shallow flow angles within the hopper 336. The design may vary depending on the particulate matter or SAP 326 being held in the hopper 336, and it may be desirable to test the properties of the material, such as the material's slip angle and angle of repose, to obtain a suitable hopper design. The design of mass flow hoppers is generally known in the art, and a skilled artisan will be able to design a suitable hopper without undue experimentation based on the teachings provided herein.

In one embodiment, the hopper has a capacity of about 1.5 $ft^3$ to about 10 $ft^3$, and more preferably about 2.25 $ft^3$ to about 6 $ft^3$, and most preferably about 3 $ft^3$. Also in a preferred embodiment, the hopper 336 discharges through an outlet having a diameter of about 4 inches to about 12 inches, and more preferably about 5 to about 9 inches, and most preferably about 7 inches. The hopper 336 may be supplied and refilled with SAP using any device and method known in the art. In a preferred embodiment, the hopper 336 is filled by a screw (or "auger") type conveyor that moves SAP from a supply source into the hopper 336. The design of such hoppers 336, conveyors and supply sources is known in the art, and a skilled artisan will be able to provide a hopper 336 for use with the present invention without undue experimentation based on the teachings provided herein.

In a preferred embodiment, the hopper 336 is derived from a SOLIDSFLOW MODEL 5007 DRY MATERIAL FEEDER. Also in a preferred embodiment, the hopper 336 is supplied and refilled from a SOLIDSFLOW MODEL SBS BULK BAG DISCHARGE STATION using a FLEXICON flexible screw (auger) conveyor, which is controlled by a SOLIDSFLOW MODEL 1200 LOSS-IN-WEIGHT CONTROLLER. All of these devices are available from SolidsFlow Corporation of Fort Mill, S.C.

The vibratory feeder 332 may be suspended from one or more, and most preferably three, scales 342 that measure the weight of the vibratory feeder 332 and its contents. The scales may be used to calculate the amount of SAP 326 that is being distributed onto the opened tow 312. Such systems are commonly known as "loss-in-weight" systems, as they continuously measure the reduction in weight of the vibratory feeder 332 as its contents are being emptied. The conveyors and supply sources that feed into the hopper 336 may also be suspended on scales so that SAP may be added to the hopper during operation, while still being able to calculate the amount of SAP being deposited onto the opened tow 312. In a preferred embodiment, the loss-in-weight measurements of the scales 342 are used with a closed-loop feedback circuit to control the amount of SAP 326 that is deposited onto the opened tow 312. Such a circuit is preferably integrated into a control system 320 that may control other features and operation of the vibratory feeder 332 and related devices. The scales 342 may also be used to determine when it is necessary or desirable to refill the hopper.

The scales 342 are preferably able to read to an accuracy that allows useful determination of the amount of SAP being deposited onto the opened tow 312. In a preferred embodiment, the scales 342 read to an accuracy of about +/−10 grams, and more preferably of about +/−1 gram, and most preferably of about +/−0.1 gram. In a preferred embodiment, the scales 342 comprise strain gauge-type load measurement cells, such as those available under the designation SOLIDSFLOW MODEL 1000 SCALE ASSEMBLY from SolidsFlow Corporation of Fort Mill, S.C. The design, construction, and use of scales suitable for use with the present invention is known in the art.

A flexible coupling 338 preferably joins the hopper 336 to the feed tray 334. The flexible coupling 338 is used to pass SAP or other additives from the hopper 336 to the feed tray 334, while simultaneously isolating the hopper 336 from the vibratory movement of the feed tray 334 and vibrator 340. The flexible coupling 338 may comprise any durable flexible material, such as canvas and other cloths, or natural or synthetic rubbers. It is preferred that the flexible coupling does not damp or impede the desired vibrating motion of the feed tray 334 and vibrator 340, and thereby impair the ideal SAP feeding. For example, if the flexible coupling 338 is too rigid, it will reduce the ability of the vibrator 340 to vibrate the feed tray 334 because it will resist deformation, effectively increasing the mass of the feed tray 334. Also, if the flexible coupling 338 is too elastically resilient, it will tend to store energy created in it when the feed tray 334 and vibrator 340 are vibrating, and return this stored energy in an uncontrolled manner (i.e., vibrate on its own) thereby creating additional uncontrolled vibrations in the feed tray 334 and vibrator 340. It also is preferred that the flexible coupling 338 be as light as possible so as to reduce the inertia that must be overcome by the vibrator 340 during operation. In a preferred embodiment, the flexible coupling 338 comprises a rubber material having a diameter and shape selected to join the outlet of the hopper 336 with the inlet chute 402 of the feed tray 334.

The feed tray 334 and vibrator 340 preferably are suspended below the hopper 336 by flexible mounts 344 that allow the vibrator 340 and feed tray 334 to move relative to the hopper 336. The flexible mounts 344 may comprise rods having flexible or pivoting couplings joining them, at each end, to the hopper 336, vibrator 340 and feed tray 334. In a preferred embodiment, the flexible mounts 344 are designed to convey a minimal amount of vertical movement or vibration to the hopper 336, which may cause the scales 342 to read inaccurately. In such a preferred embodiment, the flexible mounts 344 may be joined to one or more of the hopper 336, vibrator 340 and feed tray 334 by a dry or liquid-filled elastomeric bushing or coupling. The design and selection of such vibration- and movement-damping couplings are known in the art, and a skilled artisan will be able to select or produce an appropriate coupling system based on the teachings provided herein.

Referring now to FIG. 4, the feed tray 434 preferably comprises an inlet chute 402 that is attached to the flexible coupling 338 to receive SAP 326 from the hopper 336. A pan 404 extends away from the inlet chute 402 at a downward angle α to an outlet edge 406 of the feed tray 334. The pan 404 may also comprise multiple sections that descend at varying angles. The feed tray 334 preferably is covered along most of its length to prevent disturbances of the SAP 326 or other particulate additives. The covered portion preferably terminates at an adjustable gate 408 located near the outlet edge 406 of the feed tray 334. The adjustable gate 408 is spaced above the pan 404 and generally divides the feed tray into an upstream portion from which the SAP 326 flows and a downstream portion. The adjustable gate 408 may be operated manually, or may be opened and closed by an actuating device, such as an electromechanical, mechanical, pneumatic, or hydraulic device. Such an actuating device may optionally be controlled by a control system 320 using a closed-loop feedback algorithm or open-loop algorithm. Such actuating devices are known in the art, and a skilled artisan will be able to employ a suitable actuating device without undue experimentation. Of course, in one embodiment the gate may be a fixed gate, rather than an adjustable gate.

Figure 7:
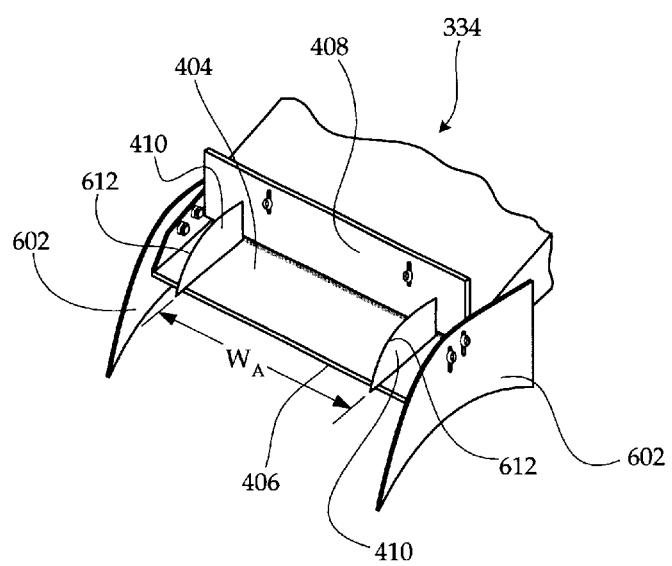
FIG. 7 is an isometric view of the outlet portion of a feed tray according to a preferred embodiment of the present invention.

In a preferred embodiment, the SAP 326 or other particulate additive material exits the feed tray 334 at its outlet edge 406 in a curtain-like stream having a consistent flow rate across its entire width. Referring to FIG. 7, the active width $W_A$ of the feed tray 334 is the width of the portion of the feed tray 334 from which the SAP 326 flows (which may be affected by the use of SAP guides 410, as described elsewhere herein), and generally corresponds to the width of the SAP flow. The active width $W_A$ may vary from one application to the next, and may be varied during operation by using, for example actuated pivoting SAP guides 410 that move together and apart under the control of a control system 320. Generally, the active width $W_A$ preferably is as approximately the same width as the opened tow 312. In one embodiment active width $W_A$ is about 2 inches to about 12 inches, and is more preferably about 3 inches to about 10 inches, and, in a particularly preferred embodiment, the active width $W_A$ is as about 3.75 inches to about 4 inches.

In other embodiments it may be desirable to vary the flow rate of the SAP 326 in particular areas to provide zoned absorbency. Referring now to FIG. 7, the pan 404 may be contoured or shaped to provide concentrated flows of SAP during operation or to otherwise control the flow of the SAP. For example, in one embodiment the pan 404 may have one or more depressions 1502 along the outlet edge 406 that effectively increase the downward angle α at the depressions 1502. In such an embodiment, the SAP 326 may tend to funnel into the depressions 1502, and those portions of the opened tow 312 that pass beneath the depressions 1502 should receive a relatively high concentration of SAP 326. In another embodiment, the pan 404 may have troughs 1504 that extend below the adjustable gate 408, effectively increasing the height h of the adjustable gate 408 at those points to increase the flow rate of SAP through the troughs 1504. Such troughs 1504 may extend to the outlet edge 406 to additionally act as depressions 1502, as described above. Other variations in the outlet edge 406 and pan 404 geometry will be apparent to those skilled in the art based on the teachings provided herein.

In one embodiment, the feed tray 434 may have more than one inlet chute 402 so that a number of different supplies of SAP may be fed into it. The supplies of SAP may comprise different types of SAP that are blended or isolated from one another using internal baffles and guides. In such an embodiment, for example, one type of SAP may be distributed to the lateral sides of the opened tow 312, and another type of SAP may be distributed to the central region of the opened tow 312. Other variations and uses of a feed tray 334 having multiple inlet chutes 402 will be apparent to those skilled in the art based on the teachings provided herein.

SAP guides 410, comprising vertical or angled strips of material, optionally may be integrated into the feed tray 334 on either side of the adjustable gate 408 to serve a number of purposes. The SAP guides are preferably attached to the pan 404, but may also be attached elsewhere to the feed tray 334 or to other objects. In a preferred embodiment, the guides contain the lateral movement of the SAP 326 so that it falls only in a center region of the opened tow 312. In another preferred embodiment, the SAP guides 410 isolate the flow of SAP 326 from turbulent airflow around the feed tray 334 to provide more even SAP distribution. The SAP guides 410 may be proximal to the outlet edge 406, as shown in FIG. 4, or may be located elsewhere on the pan 404. The SAP guides 410 may also be used to isolate or blend different supplies of SAP. In one embodiment, the SAP guides 410 may also comprise additional vertically stacked layers, in addition to the pan 404, that may contain separate flows of SAP. In a preferred embodiment, the SAP guides 410 are spaced apart by about 3.75 inches to about 4 inches to provide about a 3.75 inch to about 4 inch wide flow of SAP.

Referring now to FIGS. 5A and 5B, the feed tray 334 operates on the principle that particulate solids within them, such as SAP 326, will rest at their angle of repose until disturbed by vibrations induced by the vibrator 340. This principle of operation is more fully disclosed in U.S. Pat. No. 3,973,703 to Peschl, which is incorporated by reference herein in its entirety and in a manner consistent with the present invention (hereafter referred to herein as "Peschl"). It should be understood that, although the inventors provide various theories on the modes of operation of the vibratory feeder 332, the invention is not intended to be limited to these or other modes or theories of operation.

It has been found that the flow of the SAP 326 generally may be influenced by the properties of the SAP, the downward angle α of the pan 404, the rate of vibration of the vibrator 340, the trailing distance d of the pan 404, and the height of the adjustable gate 408. In the embodiment shown in FIG. 5A, the feed tray 334 is shown at rest, with the SAP 326 being contained within the feed tray 334. In the embodiment of FIG. 5A, the downward angle α is greater than the angle of repose of the SAP 326, and so any SAP remaining along the trailing distance d of the pan 404 slides off the pan 404 after the vibrator 340 stops vibrating. The remaining SAP 326 is caught behind a bridge 502 of SAP that forms by friction between the particles of SAP, cohesion between the SAP particles, or both. The adjustable gate height h may be adjusted to provide ideal SAP containment and control. Raising the adjustable gate 408 generally provides a greater SAP flow rate for a given vibrator vibration frequency, while lowering the adjustable gate 408 generally provides the opposite result. The adjustable gate height h preferably is adjusted to ensure that a bridge 502 forms promptly after the vibrator 340 stops vibrating the feed tray 334 to stop the flow of SAP 326 as quickly as possible.

The flow rate of the SAP generally follows the vibration rate of the vibrator 340, and stops flowing almost immediately upon shut down of the vibrator 340. Generally, faster vibrator vibration rates provide greater SAP flow rates and slower vibrator vibration rates provide a slower SAP flow rate. There is little or no appreciable time delay between changes in the vibrator frequency and the flow rate of the SAP 326, so the vibratory feeder 332 provides relatively accurate control of the SAP flow, especially when compared to known methods of distributing SAP onto opened tow 312 or fluff pulp.

It should be noted that SAP remaining on the trailing distance d of the pan 404 may continue to flow at an uncontrolled rate after the vibrator frequency changes, but such lag time has not been found to cause an appreciable detriment to the device's ability to accurately deposit SAP 326 onto the opened tow 312. If a detriment is found, however, the trailing distance d may be reduced to make the SAP flow rate follow the vibrator frequency variations more closely. Reducing the trailing distance may also increase the flow rate of the SAP for a given vibrator frequency and adjustable gate height h, as is explained in more detail in Peschl. In one embodiment, the trailing distance may be reduced to zero, and the outlet edge 406 even may be within the upstream portion of the feed tray 334 (i.e., the adjustable gate 408 may be located beyond the outlet edge 406).

In a more preferred embodiment, shown in FIG. 5B, the downward angle α may be less than the SAP's angle of repose and slip angle (i.e., the angle at which the SAP 326 will slide down the surface of the pan 404), so that when the feed tray 334 is at rest the SAP remaining along the trailing distance d stays on the pan 404. In such an embodiment, the aforementioned lag between SAP flow and vibrator frequency changes associated with the SAP located in the trailing distance d may be reduced.

Referring back to FIG. 4, it has been found that the feed tray's outlet edge 406 should be located as close as possible to the vacuum draw roll 322. Reducing the offset distance c between the outlet edge 406 and the vacuum draw roll 322 provides a number of benefits. In particular, minimizing the offset distance c allows the SAP to fall onto the opened tow 312 as quickly as possible, minimizing any redistribution or diffusion of SAP 326 that may be caused during a longer fall by turbulent air flowing around the feed tray 334 and by interaction between the SAP particles 326. Reducing the offset distance c also decreases the lag time between changes in vibrator speed 340 and changes in the amount of SAP 326 being distributed to the opened tow 312. In a preferred embodiment, the offset distance is about 0.25 inches to about 4.00 inches, and more preferably about 0.375 inches to about 1.00 inch, and most preferably about 0.50 inches.

The minimum value for the offset distance c may be affected by machine operating tolerances, such as to prevent contact between the open tow 312 or the vacuum draw roll 322 and the vibrating feed tray 334, or by other factors, such as the tolerances of the casing sheet supplies 316, 318 and opened tow 312. For example, in a preferred embodiment, the offset distance c is at least about 0.50 inches to allow passage of clumped aggregations of opened tow 312, that may be present during startup and during other operating conditions.

In a preferred embodiment that may be used with a variety of SAPs, the downward angle α, as measured relative to horizontal, is about 10 degrees to about 45 degrees, and more preferably about 12 degrees to about 30 degrees, and most preferably about 15 degrees. Also in a preferred embodiment, the adjustable gate height h is about 0.10 inches to about 1.00 inches, and more preferably about 0.125 inches to about 0.75 inches, and most preferably about 0.25 inches to about 0.50 inches. Also in a preferred embodiment, the trailing distance d is about 0.25 inches to about 8 inches, and more preferably about 2 to about 6 inches, and most preferably about 4 inches. Also in a preferred embodiment, the inlet chute 402 has a diameter of about 4 inches to about 12 inches, and more preferably about 5 to about 9 inches, and most preferably about 7 inches. In a preferred embodiment, the feed tray 334 may be derived from a SOLIDSFLOW MODEL 5000 DRY MATERIAL FEEDER, available from SolidsFlow Corporation of Fort Mill, S.C.

Figure 6:
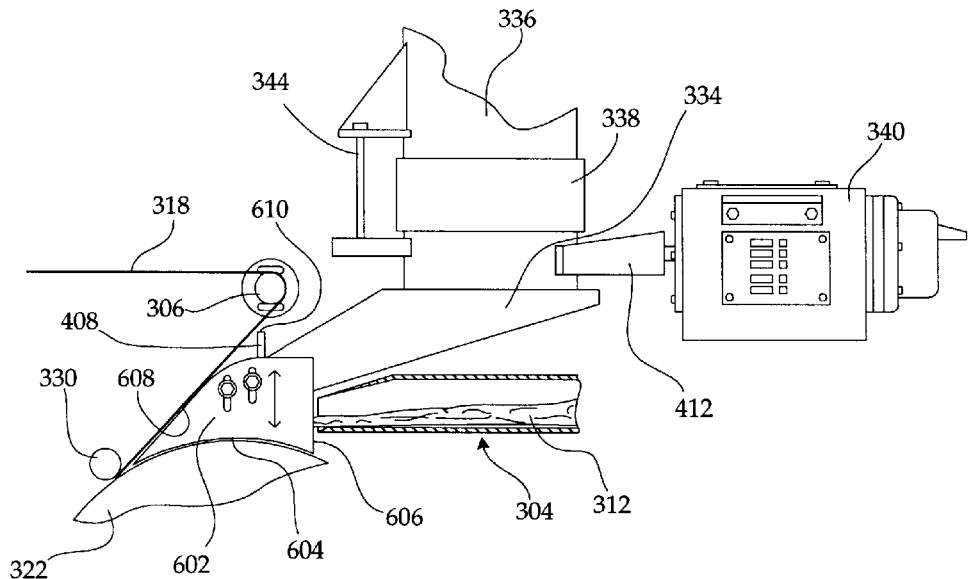
FIG. 6 is a partially cut away side view of a feed tray, vibrator and side plates according to a preferred embodiment of the present invention.

Referring now to FIGS. 6 and 7, the feed tray 334 preferably is equipped with side plates 602 that help isolate the SAP 326 and opened tow 312 from lateral airflow and may help contain the lateral movement of SAP 326 after it exits the feed tray 334. Such lateral airflow and other airflow may disturb the desired distribution of SAP onto the opened tow 312. The side plates 602 are preferably oriented approximately parallel to the machine direction of the opened tow 312 (i.e., within about 20 degrees of parallel) and sized to substantially reduce or block air from flowing laterally into the area beneath the feed tray 334. Preferably, a first edge 604 of each side plate 602 is located proximal to the vacuum draw roll 322 (or other similar drawing device); and a second edge 606 of each side plate 602 is located proximal to the forming jet assembly 304. The side plates 602 are preferably shaped and sized so that they do not strike any other parts of the machine as they are vibrated back and forth. A third edge 608 of each side plate 602 preferably is adapted to conform to the second casing sheet supply 318 to help prevent lateral airflow from above the feed tray from encroaching upon the supply of SAP 326. In such an embodiment, it also may be desirable for the top edge 610 of the adjustable gate 408 to be proximal to the second casing sheet supply 318 to further reduce the amount of air that flows in to potentially disturb the SAP 326. The SAP guides 410 may also have an edge 612 contoured to be adjacent to the second casing sheet supply 318 to further inhibit the development of undesirable airflow near the SAP 326. The side plates 602 preferably may be adjusted in at least the vertical direction, as indicated by the double-headed arrow in FIG. 6. In other embodiments, the side plate 602 may be attached to something other than the feed tray 334, but in such embodiments, care should be taken to prevent the moving feed tray 334 from striking the side plates 602 during operation.

Referring back to FIG. 4, the vibrator 340 is used to initiate and modulate the flow of SAP 326 out of the feed tray 334. The vibrator 340 vibrates the feed tray 334 by moving it back and forth in the direction of vibration V, as indicated by the double-headed arrow in FIG. 4. In a preferred embodiment, both the pitch p and frequency of the vibrator 340 may be adjusted to modulate the flow of SAP 326. It has been found that increasing the vibrator's pitch p (i.e., the distance traversed by the vibrator during each cycle) generally increases the SAP flow rate, and vice-versa. Also, as noted before, it has been found that increasing the vibrator's frequency generally also increases the SAP flow rate, and vice-versa.

The effectiveness of the vibrator 340 and amount of control provided by the vibrator 340 are affected by the weight and rigidity of the feed tray 334. If the feed tray 334 is too heavy, its inertia will resist the forces imparted upon it by the vibrator 340, and the vibrator 340 may not be able to accelerate and decelerate it back and forth to create the desired pitch p distance or frequency vibrations. If the feed tray 334 is not rigid enough, it will flex as the vibrator 340 imparts forces on it. As the feed tray 334 flexes, it absorbs the energy that was intended to move the feed tray 334 and does not accurately follow the path intended by the vibrator 340. The energy absorbed by a flexible feed tray 334 may be released in the form of undesirable variations in the intended pitch p and frequency of vibration. It has been found that it is generally desirable to make the feed tray 334 as light and as rigid as possible in order to provide the greatest amount of control of the SAP flow.

In a preferred embodiment, the vibrator 340 is coupled to the feed tray 334 through a coupling 412. In order to provide accurate transmission of the vibrator's vibrations to the feed tray 334, the coupling 412 should be rigid in the vibration direction V, and the coupling 412 preferably has a box-like shape or C-shape. Also in a preferred embodiment, the inlet chute 402, which may comprise a relatively large open space that may be susceptible to undesirable flexing, is reinforced with a structural member, such as a tubular brace 414 aligned in the vibration direction V. In an embodiment in which the inlet chute has a diameter of about 7 inches it has been found that a tubular brace 414 of about 1 inch diameter is suitable to reduce undesirable flexure in the inlet chute 402 without adversely affecting the flow of SAP through the inlet chute. In other embodiments, in which the inlet chute 402 contains baffles or other internal flow-directing or flow-controlling structures, these structures may also serve to increase the feed tray's rigidity, making it unnecessary to reinforce the inlet chute 402.

As noted before, the vibrator 340 and feed tray 334 are suspended beneath the hopper 336 by flexible mounts 344 that allow both the vibrator 340 and the feed tray 334 to move independently of the hopper 336. As such, as the vibrator 340 vibrates the feed tray 334 back and forth, the vibrator 340 itself may also move back and forth. In a preferred embodiment, the mass of the vibrator 340 is significantly greater than the combined mass of the feed tray 334 and the SAP 326 contained therein, and so the movement of the vibrator 340 will be insignificant relative to the movement of the feed tray 334. In such an embodiment, the vibrator's pitch p will be almost entirely converted into movement of the feed tray 334 (as is shown in FIG. 4). If, however, the vibrator 340 does experience a significant amount of movement, more of the pitch p will be converted into the vibrator's movement, and less of the pitch will result in movement of the feed tray 334. This reduction in the movement of the feed tray 334 may result in less effective SAP distribution and control. If it is found that the movement of the vibrator negatively affects the SAP distribution and control, the vibrator's movement may be restricted, or the pitch p may be increased to increase the effective movement of the feed tray 334. Other measures may also be taken to counteract such negative affects. Those skilled in the art will be able to measure or calculate the movement of the vibrator 340 and feed tray 334 and make accommodations in the design of the apparatus for such movements using the teachings provided herein.

In a preferred embodiment, the vibrator 340 comprises an electromagnetic vibrator, such as those supplied by Eriez, Corporation of Erie, Pa. as Model Number 30A, part number 3N-56743. Such a vibrator may be selected to be driven by any available power source, such as a 115 volt, 60 Hz power source. The vibrator may also require specific support or drive hardware and software, such as an Eriez VTF signal following controller board that is supported by and AB SLC 0-20 mA analog card, available from Allen-Bradley Company of Milwaukee, Wis. Other vibrators 340 may also be used, such a rotary motor that is configured to provide cyclical lateral movement or vibrations to the feed tray 334. Other useful vibrators 340 include pneumatic, magnetic, electric and hydraulic actuators, and the like, as long as they can provide the necessary forces to vibrate the feed tray 334 at the desired pitch p and frequency. Electromagnetic vibrators are preferred, as they typically provide relatively controllable movement and consume less energy than other devices.

In one embodiment that should be suitable for dispensing a variety of SAP materials, the vibrator 340 may be operated from a standstill (zero Hz) up to about 430 Hz, and more preferably up to about 520 Hz, and most preferably up to about 600 Hz. In a preferred embodiment that should be suitable for dispensing a variety of SAP materials, the frequency is approximately constant, and the flow rate of the particulate matter is controlled by modulating the vibrator's pitch. In such a preferred embodiment, the vibrator frequency is about 60 Hz, and the pitch p of the vibrator variable between about 0.01 inches to about 0.125 inches, and more preferably about 0.02 inches to about 0.10 inches, and most preferably about 0.04 inches to about 0.08 inches. Such adjustments may be obtained, for example, by varying the voltage of the vibrator between about 0 and about 90 volts.

Such a vibratory feeder 332 may be adapted to provide a high volume of SAP flow, and may be used at relatively high manufacturing line speeds. It is anticipated that a vibratory feeder produced according to a preferred embodiment of the present invention may be used with an assembly line producing diapers at a rate in excess of 600 products per minute. The vibratory feeder 332 preferably can feed superabsorbent polymer or other additives at a rate of about 10,000 grams per minute (g/min) to about 20,000 g/min, and more preferably at a rate of about 12,500 g/min to about 17,500 g/min, and most preferably at a rate of about 15,000 g/min. In a preferred embodiment, the hopper 336 is fed by a screw-type conveyor or other conveyor that has a capacity to maintain a useful level of SAP 326 in the vibratory feeder 332. The conveyor may have a feed rate that is less than the maximum feed rate of the vibratory feeder 332, so long as the average feed rate of the vibratory feeder 332 does not exceed the average feed rate of the conveyor.

Superabsorbent polymers and other particulate additives can be relatively expensive, and so it is often desirable to minimize the amount of SAP that is placed in the core and to "zone" such additives only where they are most beneficial for the final product. Such zoning is also particularly beneficial in tow-based absorbent cores because the lack of fluff pulp in such cores may reduce the overall wicking capability of the core, making it more important to place the SAP closer to the location where fluid is likely to strike the garment. In a preferred embodiment, the vibrator 340 is controlled by a control system 320 to provide a desirable distribution of SAP 326 into the opened tow 312. In one preferred embodiment, such a control system 320 may be used to operate the vibrator 320 to deposit a steady stream of SAP 326 onto the opened tow 312 to provide a uniform opened tow/SAP mixture in the absorbent cores that are ultimately formed by the process. In another preferred embodiment, the control system may cyclically increase and decrease the pitch p and/or frequency of the vibrator 340 to deposit a pulsating supply of SAP 326 to the opened tow 312, thereby providing the absorbent cores with targeted concentrations of SAP that provide the garment 10 with zoned absorbency. Preferably, the control system 320 uses a closed-loop feedback method that considers various factors in determining how much SAP to distribute at any given moment. The control system 320 is discussed in greater detail with reference to FIGS. 16–21.

In a preferred embodiment, the control system 320 is provided with information about how fast the assembly line is running by using, for example, a tachometer 346 on the vacuum draw roll 322 or by any other suitable line speed measuring device. By integrating such a line speed measuring device into the control system 320, the control system 320 may be programmed to increase or decrease the pitch p or frequency f of the vibrator 340 to vary the SAP flow rate as the product manufacturing rate changes, thereby providing all of the products with the proper amount of SAP, regardless of the assembly line speed. Such a capability provides a lower rate of product rejection during transitional phases, thereby improving the overall efficiency of the manufacturing process.

In another preferred embodiment, the output of the scales 342 is integrated into the control system 320. By considering the weight of the SAP being distributed, as measured by the scales 342, the control system 320 may programmed to modulate the vibrator 340 to accurately distribute SAP at the desired flow rate. In such an embodiment, the control system 320 may also accommodate for deviations in the flow characteristics of the SAP particles to continue to provide an even flow, such as by increasing the vibration pitch and/or frequency if it is found that the SAP is not flowing as rapidly as expected, and vice-versa. Such deviations may be caused by typical variations in the shape, size, humidity, density, or other features of the SAP, or may be caused when a different SAP product is used in a machine that was originally set up for another type of SAP or set up for a SAP provided by a different supplier.

The control system 320 may also be adapted to stop distributing SAP in the event that a fault is detected in the processing line. For example, if a fault detection circuit tied into the control system 320 determines that one or more products will be defective upon completion, the flow of SAP may be stopped so that the defective products will not receive SAP. In such an embodiment, it may be desirable to produce the absorbent cores of the garments as late as possible in the manufacturing process in order to detect as many defects as possible before preparing the absorbent core 6 for each product.

In one embodiment, a SAP concentration detection device 350 may be integrated into the control system 320 to provide further detection and control capabilities to the control system 320. The concentration detection device 350 may be located to measure the amount and/or location of SAP in the assembled absorbent core composite 348. If the amount of location of the SAP is not present as desired, the concentration detection device 350 may signal this to the control system 320 so that appropriate corrections in the SAP feed rate may be made.

The flow rate of the SAP may also be controlled by a control system 320 by actively adjusting the height h of the adjustable gate 408 during operation. As noted before, the adjustable gate 408 may be raised and lowered during operation to increase and decrease, respectively, the flow rate of the SAP 326. Such adjustments may also be made to provide a cyclically fluctuating amount of SAP to the opened tow 312 to create targeted regions of relatively high SAP concentration for zoned absorbency. In such an embodiment, the control system 320 may operate the adjustable gate 408 in conjunction with the scales 342, tachometer 346, concentration detection device 350, or other sensors to provide closed-loop feedback control of the SAP flow. A suitable actuation device for cyclically raising and lowering the adjustable gate 408 preferably does not cause excessive vibrations or other movements that may cause the scales 342 to read inaccurately.

Figure 9:
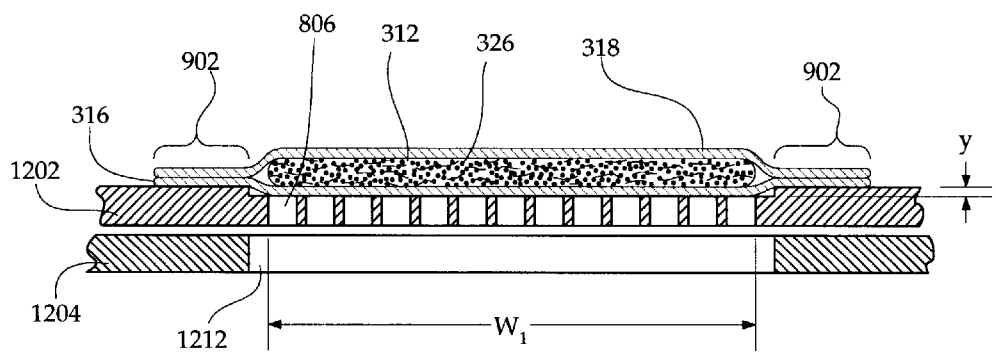
FIG. 9 is an isometric view of a combining drum according to a preferred embodiment of the present invention.

Referring now to FIG. 9, it has been found that a "combining drum"-type vacuum draw roll 800 may be advantageously used in conjunction with vibratory feeders 332, such as those described herein, or, alternatively, with other SAP feed devices and methods, such as those that are known in the art. The combining drum 800 is characterized in that several or all of the parts that eventually form the absorbent core 6 of the garment 10 are assembled in a continuous motion around all or part of the combining drum's circumference. In a preferred embodiment, the combining drum 800 combines the first casing sheet supply 316, opened tow 312, SAP 326 and second casing sheet supply 318 (i.e., various constituent parts of the core composite 348, which may, of course, include other parts) in a substantially continuous operation as they are conveyed by the combining drum 800. Each of the parts may be conveyed to the combining drum 800 separately and then joined together into an integrated structure, or alternatively, some of the parts may be joined to one another prior to contact with the combining drum 800. For example, an additional layer 20 may be affixed to either side of one or both of the first and second casing sheet supplies 316, 318 before the supply is provided to the combining drum 800.

As noted before, a preferred combining process has been generally described elsewhere herein with reference to Locations A, B, C and D of FIG. 3. The operation of the combining drum 800 described herein is relatively simple compared to many known core-forming apparatus, and may be adapted to operate at high line speeds. For example, it is anticipated that the combining drum 800 may be adapted to operate with an assembly line producing in excess of 600 diapers per minute.

In a preferred embodiment the combining drum 800 has a generally cylindrical surface 802 with a vacuum surface 804 forming a circumferential belt on the cylindrical surface 802. The vacuum surface 804 comprises one or more holes 806 through which a vacuum is applied to the various parts of the core composite 348. The holes 806 in the vacuum surface 804 may be formed by any means known in the art, such as drilling, machining, casting and so on. In a preferred embodiment, the holes 806 have a diameter of about 0.0625 inches to about 0.75 inches, and more preferably of about 0.125 inches to about 0.625 inches, and most preferably of about 0.25 inches to about 0.50 inches. Also in a preferred embodiment, the holes may be spaced from one another by a center-to-center distance of about 0.10 inches to about 1.00 inch. The holes may be spaced in a rectilinear array, as staggered rows, or in any other pattern that conveys the desired amount of vacuum. The vacuum surface 804 also may comprise any other relatively rigid foraminous structure, such as one or more mesh screens or removable perforated plates that are affixed to openings in the cylindrical surface 802. In a preferred embodiment, the combining drum 800 may also comprise landing areas 808 on either side of the vacuum surface 804 which may be treated to enhance their ability to grip the first and second casing layer supplies 316, 318. A vacuum is applied to the combining drum 800 through a vacuum port 810.

Figure 10:
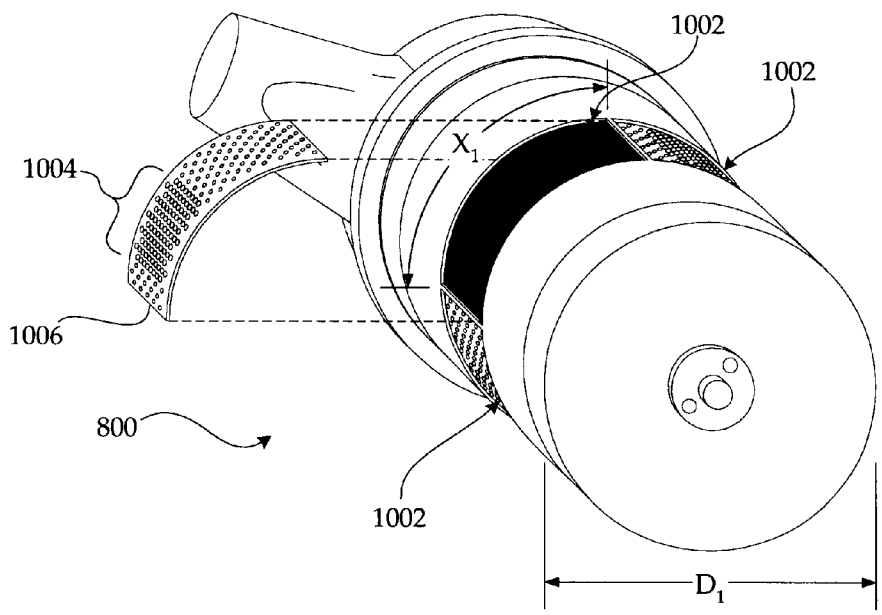
FIG. 10 is a sectional view of the vacuum surface of a combining drum according to a preferred embodiment of the present invention, shown operating with the core composite adjacent the vacuum surface.

Referring now to FIG. 10, there is shown a sectional view of the vacuum surface 804 region of a combining drum 800 as is appears just after combining the first casing sheet supply 316, opened tow 312, SAP 326 and second casing sheet supply 318 into an integrated core composite 348. The width $W_1$ of the vacuum surface 804 (as measured in a direction parallel to the rotational axis of the combining drum 800) preferably corresponds approximately to the width of the opened tow 312 and to the width of the portion of the feed tray 334 from which SAP 326 is provided. The first and second casing sheet supplies 316, 318 are preferably wider than the opened tow 312, and their excess width is located in side areas 902 that overlie the landing areas 808. The first and second casing sheet supplies 316, 318 preferably are joined to one another in their side areas 902 by adhesive bonding, other methods described elsewhere herein or by other methods known in the art. As noted elsewhere, a lay on roll 330 may be used to help join the first and second casing sheet supplies 316, 318 by use of pressure, crimping nodules, and the like.

In a preferred embodiment, the vacuum surface 804 is recessed in the cylindrical surface by a depth y of less than about 0.50 inches, and more preferably by less than about 0.10 inches, and most preferably by about 0.030 inches. It has been found that having a slight increase in the diameter of the combining drum 800 on either side of the vacuum surface 804 (i.e., a recessed vacuum surface 804) helps keep the first casing sheet supply 316 stretched across the combining drum 800 during operation.

The vacuum surface width $W_1$ may be selected to provide certain benefits to the garment into which the core composite 348 is being integrated. In one embodiment, the core composite may be integrated into the garment in a flat state, in which case it may be desirable to make the vacuum surface width $W_1$ and the width of the opened tow 312 equal to the desired width of the garment's absorbent core 6. However, the core composite 348 may be stretched, folded, or otherwise resized during manufacture, in which case the vacuum surface width $W_1$ should be correspondingly adjusted. In a preferred embodiment, the core composite 348 is folded at least once before being integrated into the garment. Folded absorbent cores have been discussed in more detail elsewhere herein. In a preferred embodiment, the vacuum surface width $W_1$ is about 1.75 inches to about 12 inches, and more preferably about 2.75 inches to about 10 inches, and most preferably about 3.75 inches. In order to reduce SAP loss during core formation, the vacuum surface width is preferably slightly narrower (about 0.10 inches on either side) than the width of the supply of opened tow 312 to promote a slight inward migration of SAP away from the side areas 902.

As noted before, it has been a continuing challenge to provide the desired distribution of SAP within the absorbent cores 6 of absorbent garments 10. It has been found that a combining drum 800 as described herein may be beneficially used to help provide such desired SAP distributions. Cellulose acetate opened tow 312 and other types of low density fibrous opened tow structures allow a relatively large amount of air to pass through them compared to conventional fluff pulp materials, and the location of the SAP 326 may be effectively controlled by modulating the amount and position of the vacuum applied to the SAP/opened tow mixture. It has been found that the distribution of the SAP can be more easily controlled with tow/SAP cores than with fluff/SAP cores. As air passes through the opened tow 312 into the vacuum it conveys the SAP 326 through the fibrous structure, and the SAP particles 326 generally tend to concentrate more densely at areas having a high vacuum. Also, as the vacuum is increased, the SAP particles 326 generally move closer to the surface of the opened tow 312 that is adjacent the combining drum 800. The degree to which the SAP migrates towards the high vacuum areas may also be affected by the duration of time that the vacuum is applied to the SAP 326. The vacuum also helps prevent SAP 326 from escaping out of the opened tow 312 during manufacturing. It has been found that a desirable mixture of SAP 326 within the opened tow 312 and reduced SAP loss may be produced using a vacuum of about 2.50 inches of water to about 20 inches of water, and more preferably of about 3.75 inches of water to about 12.5 inches of water, and most preferably of about 5.0 inches of water. The vacuum may be pre-set or may be manually or actively controlled by a control system 320 using an open-or closed-loop feedback system.

In addition to being useful for providing a homogeneous dispersion of SAP 326 in the opened tow 312, a combing drum 800 as described herein may also be used to accomplish various other desirable SAP distribution patterns. In one embodiment, the vacuum level may be modulated to provide a desirable depth of SAP penetration throughout the opened tow 312 or only in discrete areas of the opened tow 312. In other embodiments, the combining drum 800 may be adapted to provide machine direction (MD) and cross-machine direction (CD) zoning of the SAP particles 326 that provide the garment 10 with zoned absorbency. The machine direction is the direction in which a part or assembly moves during processing, and the cross-machine direction is perpendicular to the MD. The machine direction generally corresponds to the longitudinal dimension 100 of the fully-assembled garment 10 (see FIG. 1), and the cross machine direction corresponds to the lateral dimension 102 of the garment, however other relationships may also be used and are within the scope of the present invention.

Figure 11:
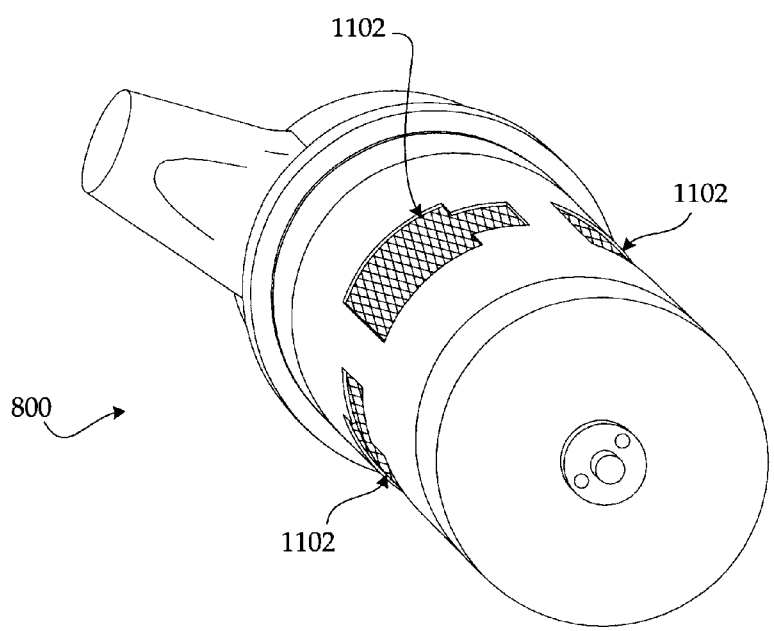
FIG. 11 is a partially exploded isometric view of another combining drum according to a preferred embodiment of the present invention.

Referring now to FIG. 11, regions of high SAP concentration, and thus greater absorbency, may be provided in the MD and CD by making the vacuum surface 804 with particularly designed target regions 1002 that convey a greater amount of vacuum to portions of the opened tow 312. Such target regions 1002 may have larger holes and/or a greater concentration of holes in those areas where a greater concentration of SAP 326 is desired. The larger amount of open space provided in such regions will allow a greater amount of airflow into the vacuum, and thus cause a greater amount of SAP to migrate to those areas. For example, in the embodiment of FIG. 11, the region 1004 has a greater concentration of larger holes, which should provide a SAP concentration in the portion of the core composite 384 adjacent region 1004. The particular pattern of SAP concentration may be adjusted by making each of the target regions 1002 from a removable plate 1006 having the desired hole pattern. Substitute plates 1006 may be easily machined to provide different hole patterns and zoned absorbency patterns.

In another embodiment, shown in FIG. 11, the vacuum surface 804 may be separated into discrete target regions 1102, which may have varying widths, to provide zones of high and low MD and CD SAP concentrations.

In an embodiment in which the combining drum 800 has target regions 1002, 1102 for providing zoned absorbency, the combining drum diameter $D_1$ should be selected so that the corresponding parts of each target regions 1002, 1102 are spaced from one another around the circumference of the combining drum 800 by a distance corresponding to the absorbent core length $X_1$. By using such a spacing, each target region 1002, 1102 will create a targeted zone of SAP that will be properly located in each absorbent core 6 that is cut from the core composite 348.

It should be understood that by providing a distance between corresponding parts of each target region 1002, 1102 that is approximately equal to a core length $X_1$, the circumference of the combining drum 800 will be sized to equal a whole number multiple of the core length $X_1$. At a minimum, the circumference can equal one core length $X_1$, but in such an embodiment, the various parts of the core composite 348 will be in contact with the vacuum for relatively little time, which may lead to inadequate SAP distribution or other forming problems. Smaller diameter drums may also be subject to greater vibration. These problems may become exacerbated when the vacuum drum 800 is used with higher speed assembly lines. Problems may also be exist with larger drum diameters. For example, the manufacturing tolerances for a larger diameter drum may be less precise. In addition, as the size of the drum increases the amount of startup waste may increase, particularly if a greater amount of vacuum is required for the larger drum, leading to longer vacuum stabilization times. Larger drums that require greater amount of vacuum also may require more power to produce the necessary vacuum. It will be understood that these considerations also apply to embodiments of the invention in which the combining drum 800 does not have target regions 1002, 1102, such as in the embodiment depicted in FIG. 9.

It is preferred, therefore, that the drum diameter $D_1$ be selected so that the drum's circumference is large enough that the parts of the core composite 348 are in contact with the vacuum long enough to properly distribute the SAP without excessive vibrations, but small enough to provide the required precision and a minimal amount of startup waste. It has been found that in a preferred embodiment, the diameter $D_1$ is selected so that the circumference is equal to between three and seven core lengths $X_1$. In a preferred embodiment, the combining drum 800 (whether it has target regions 1002, 1102 or not) has a diameter $D_1$ of about 6 inches to about 28 inches, and more preferably of about 9 inches to about 20 inches, and most preferably of about 12 inches. In this embodiment, the number of wasted cores caused by vacuum hysteresis or other startup-related issues has been found to be about 5 products per startup, as compared to up to about 50 products per startup with conventional core forming processes. It has also been found that providing the necessary vacuum to such a combining drum 800 requires about 10 horsepower to 20 horsepower, whereas conventional core forming systems require up to about 400 horsepower, and so a significant power savings is provided.

Figure 15:
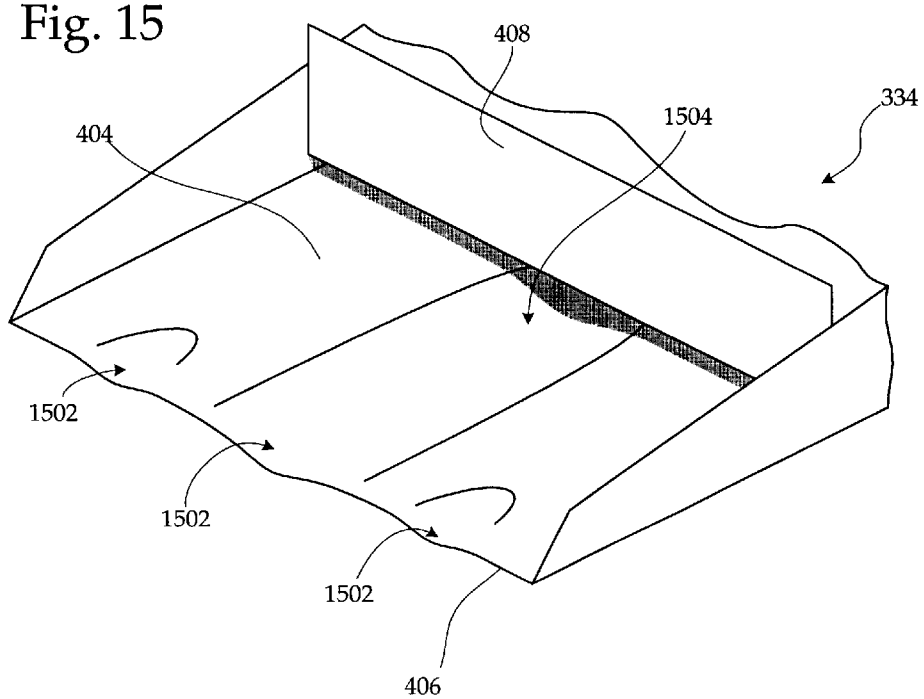
FIG. 15 is a partially cut away view of the combining drum assembly of FIG. 13, shown with the outer drum partially removed.

Referring now to FIGS. 13 through 15, a preferred embodiment of the combining drum is shown in which the combining drum 800 may be configured to apply a vacuum to the parts of the core composite 348 only through a portion of the drum's rotation. The combining drum 800 of a preferred embodiment comprises an outer drum 1202 that is positioned to rotate about a fixed inner drum 1204 by, for example, being affixed to an axle 1208 that passes through rotary bearings 1210 in the inner drum 1204. Such bearings 1210 may be equipped to reduce or prevent the leakage of the vacuum through them. A vacuum is applied to the space 1206 inside the inner drum by a vacuum port 810. The vacuum is conveyed to the outer drum's vacuum surface 804 by way of one or more passages 1212 through the inner drum 1204 that are preferably located subadjacent the path of the vacuum surface 804 of the outer drum 1202 to maximize the strength of the vacuum applied through the vacuum surface 804. It will be understood by those skilled in the art that the inner drum 1204 may be replaced by any vacuum chamber having one or more passages 1212 that convey a vacuum to a location subadjacent all or part of the vacuum surface 804.

Only those portions of the vacuum surface 804 that are immediately adjacent the passages 1212 receive a vacuum, so the duration and location of the vacuum's application may be modified by changing the size, number, or location of the passages 1212. Referring specifically to FIG. 14, the passages 1212 may be positioned through an arc of the inner drum 1204 that defines a vacuum zone $\Theta_V$. The leading edge of the vacuum zone 1302 is preferably located proximal to the point at which the first casing sheet supply 316 contacts the combining drum, which is designated as Location A in FIG. 3. The trailing edge of the vacuum zone 1304 is preferably located beyond (as the drum rotates) the point at which the second casing sheet supply 318 contacts the combining drum 800, which is designated as Location D in FIG. 3. Referring now to FIG. 15, it can be seen that those portions of the vacuum surface 804 that are not adjacent the passages 1212 are effectively cut off from the pull of the vacuum. After the core composite 348 passes the trailing edge of the vacuum zone 1304 and reaches this blocked-off area it is released from the vacuum's hold and conveyed to other parts of the assembly line.

The size of the vacuum zone $\Theta_V$ may vary depending on where the various parts are desired to be assembled to form the core composite 348. In a preferred embodiment, the vacuum zone $\Theta_V$ is about 45 degrees to about 180 degrees, and more preferably is about 90 degrees to about 160 degrees, and most preferably is about 140 degrees.

Various devices may be employed with the combining drum 800 to modulate the location and amount of vacuum applied to the core composite 348. In one embodiment, shown in FIG. 14, internal sleeves 1306 or other valving mechanisms may be used to adjust the points at which the vacuum zone $\Theta_V$ begins and ends. In another embodiment, shown in FIG. 13, other internal sleeves 1214 or other valving mechanisms may be used to narrow or widen the width of the vacuum zone $\Theta_V$, thereby effectively narrowing and widening the width $W_1$ of the vacuum surface 804. In still another embodiment, an internal sleeve or other valving mechanism may be used to reduce the vacuum level within all or part of the inner drum 1204. Any of such sleeves and valving mechanisms may be actuated by a control system 320 under the guidance of an open- or closed-loop feedback system. Greater or lesser amounts of vacuum may also be applied in discrete portions of the vacuum zone $\Theta_V$. Other designs will be obvious to one skilled in the art based on the teachings provided herein.

A combining drum 800, as described herein, may be used with any SAP feeding device that deposits SAP onto opened tow or other fibrous materials. The embodiments of the combining drum 800 described herein have been found to be particularly useful when used in conjunction with the vibratory feeder 332 as described herein.

The vibratory feeder 332 and combining drum 800 offer several advantages over prior art SAP depositing systems. In particular, the vibratory feeder 332 provides improved control over the volume and placement of the SAP 326 in the opened tow, allowing greater control over the SAP distribution (and zoned absorbency) during transitional phases, such as during machine startup, stopping and other speed changes, leading to fewer rejected products during such times. In addition, the vibratory feeder 332 and combining drum 800 provide improved SAP penetration into the opened tow 312 or other core material and an improved ability to selective position the SAP to provide desirable zoned absorbency. The vibrator feeder 332 and combining drum 800 also provide easier operation, as the various features of each device may be integrated into a control system 320. Still further, the vibratory feeder 332 and combining drum 800 are relatively simple and reliable devices that require little maintenance or cleaning, thereby reducing the operating cost of the machine. Another advantage of the vibratory feeder and combining drum 800 is that they may be operated at high line speeds without detriment to the product quality. Other benefits will be apparent to those skilled in the art based on the teachings provided herein.

Referring now to FIGS. 16–21, the control system 320 is illustrated in greater detail in accordance with at least one preferred embodiment of the present invention. Although the control system 320 is referred to herein in the singular, it should be understood that a number of independent control systems 320 may be used for various parts of the machinery, and these various systems are referred to collectively herein as a single control system 320. The control system 320 may comprise any electrical control apparatus that may be configured to control one or more variables based on the measurement of one or more inputs.

In a preferred embodiment, the control system 320 includes a programmable logic control (PLC) device 1610 having an easily used human-machine interface (HMI) 1620, as are known in the art. PLC devices often have numerous advantages over other devices that may be configured to operate as the control system 320, such as personal computer-based control boards and the like. One advantage is that PLC devices generally are more robust in the typical operating environment of the vibratory feeder 332. Another advantage is that PLC devices tend to cycle faster than other control devices, thereby allowing PLC devices to respond faster to input stimuli. Additionally, PLC devices often are vendor-independent, since the underlying operating instructions of a PLC device often can be updated and/or replaced onsite. As a result, PLC devices tend to be less expensive to operate and maintain, as well as upgrade.

The control system 320 can be adapted to operate as a closed or open loop feedback control circuit to control the operation of one or more elements of the vibratory feeder 332. Input from the level meter 314, one or more scales 342, the tachometer 346, the SAP concentration device 350, and other types of sensors may be used individually or in combination to control one or more operations of the vibratory feeder 332.

One operation of the vibratory feeder 332 that may be controlled by the control system 320 includes the rate at which fibrous material is supplied, and preferably the rate at which opened tow 312 is supplied. Input from the level meter 314 representing the rate of consumption of opened tow 312 can be provided to the control system 320. By comparing this actual rate of consumption to a desired rate of consumption, the control system 320 can increase or decrease the rotational speed of the vacuum draw roll 322 to increase or decrease the actual rate of consumption of opened tow 312, as desired. Likewise, loss-in-weight input from one or more scales 342 can be used to provide input regarding the speed at which SAP 326 is provided to the hopper 336. The control system 320 can use this information to prevent overflow or underflow of the hopper 336, such as by increasing or decreasing the rotational speed of an auger (not shown) used to convey SAP 326 to the hopper 336.

Likewise, line speed input from the tachometer 346 or other line speed sensing devices can be used by the control system 320 to determine the line speed and adjust the rate at which SAP 326 is deposited into the opened tow 312. The term "line speed," as used herein, generally refers to the rate of an assembly line that utilizes the vibratory feeder 332. The line speed can be measured as the rate at which opened tow 312 is conveyed under the feeder tray 334 and/or the rate at which the core composite 348 is produced by the vibratory feeder 332 and can be expressed in terms of product per minute or feet per minute. An exemplary method to determine the line speed can include using the tachometer 346 to measure the rotational velocity of the vacuum draw roll 322 used to convey the opened tow 312 and subsequently the core composite 348, and then convert this rotational velocity to a linear speed. Other methods of determining the line speed can be developed by those skilled in the art, using the guidelines provided herein.

Similarly, a measurement of the concentration of SAP 326 in the core composite 348 can be obtained by the SAP concentration device 350 and used by the control system 320 for feedback control of the deposition of SAP 326 into the opened tow 312. For example, the SAP concentration device 350 can include a sensor capable of measuring the dielectric effect caused by SAP 326 in the core composite 348. A change in the concentration of SAP 326 results in a change in the dielectric effect measured by the SAP concentration device 350. Accordingly, the dielectric effect can be measured to determine the change in concentration of SAP 326 along the length of the core composite 348 as it passes by the SAP concentration device 350. This change in concentration information then can be used by the control system 320 to modify the operation of the vibratory feeder 332, as necessary. To illustrate, if the core composite 348 is to have "zoned" absorbency, where more SAP 326 is placed in certain locations than others of the absorbent core 6, then the SAP concentration device 350 could be adapted to verify that the SAP 326 is being deposited at the correct concentration in the desired locations of the core composite 348. A more detailed description the SAP concentration device 350 is found in the U.S. patent application Ser. No. 10/046,206, entitled "System and Method for Phasing the Targeting of Superabsorbent Particles in Absorbent Cores", and bearing attorney docket No. 53394.000552.

In at least one embodiment of the invention, the control system 320 is used to control the vibratory motion of the vibrator 340. The term "vibratory motion," as used herein, refers to either the pitch (p) at which the vibrator 340 vibrates, the frequency (f) at which the vibrator 340 vibrates, or both. As noted previously, the pitch and/or frequency of the vibrator 340 substantially correlates to the deposition rate of SAP 326 from the feeder tray 334. Accordingly, by controlling the vibratory motion of the vibrator 340, the control system 320 can control the deposition rate of SAP 326 to synchronize the SAP deposition rate with other operations related to the operation of the vibratory feeder 332, such as the rate of supply of opened tow 312, and the like. Likewise, it may be beneficial to distribute SAP 326 into the opened tow 312 such that the resulting core composite 348 has zoned absorbency, as discussed above. In this case, the flow rate of SAP 326 can be increased and/or decreased as the opened tow 312 passes under the feeder tray 334 to generate zoned areas of increased or decreased concentrations of SAP 326 by increasing and/or decreasing the pitch/frequency of the vibrator 340.

To control the vibratory motion of the vibrator 340, the PLC device 1610 (a preferred embodiment of the control system 320) preferably transmits a signal to the vibrator 340 representative of the desired pitch (p) or frequency (f). Alternatively, the PLC device 1610 sends data representative of the desired pitch and/or frequency to a control board, and the control board then converts the data into a signal that is provided to the vibrator 340. For example, the vibrator 340 can include an electromagnetic vibrator controlled by an Eriez VTF signal following controller board supplied by Eriez, Corporation of Erie, Pa. In this case, the PLC device 1610 could send the representative data in a digital format to an AB SLC 0-20 mA analog card, available from Allen-Bradley Company of Milwaukee, Wis. The AB SLC 0-20 mA analog card then can convert the digital data to an analog signal and provide the analog signal to the Eriez VTF signal following controller board. Based on the analog signal provided by the analog card, the Eriez VTF signal following controller board controls the desired vibratory motion of the electromagnetic vibrator (vibrator 340) accordingly. Although, as illustrated in the above discussion, the use of the PLC device 1610 to control the vibrator 340 is preferred due to certain benefits disclosed herein, other control devices known in the art may be used without departing from the spirit or the scope of the present invention.

Two exemplary mechanisms to control a desired vibratory motion of the vibrator 340 are illustrated with reference to FIG. 16. One mechanism of controlling the vibratory motion of the vibrator 340 is to provide a separate signal for each property of the vibratory motion to be controlled, as illustrated with mechanism 1625. As illustrated, one or both of inputs 1626, 1627 can be provided to the vibrator 340 directly from the PLC device 1610 or from a controller card or other device connected the PLC device 1610 and the vibrator 340. The inputs 1626, 1627 can include analog signals representative of a desired pitch (p) and frequency (f), respectively. For example, the inputs 1626, 1627 can be adapted to provide a DC voltage signal having a range from 0 to 10 Volts DC (VDC) corresponding to a range of 0% to 100% of a maximum pitch and frequency, respectively.

Alternatively, as illustrated with mechanism 1628, a single signal 1629 representing two or more properties (i.e., pitch and frequency) of the vibratory motion can be provided to the vibrator 340. For example, signal 1629 can include an alternating current voltage (VAC) signal, where the amplitude of the signal corresponds to the desired pitch of the vibrator 340 and the frequency of the VAC signal corresponds to the desired frequency of the vibrator 340. The vibrator 340, or a controller board connected to the vibrator 340, then can reference this signal to generate the desired vibratory motion. Although two exemplary mechanisms have been discussed, those skilled in the art are capable developing other mechanisms to direct the vibratory motion of the vibrator 340, using the guidelines provided herein.

FIGS. 17–21 illustrate a method to prevent waste of SAP 326 and/or core composite 348 during the transitory periods of the assembly line utilizing the vibratory feeder 332 in accordance with a preferred embodiment of the present invention. In general, conventional absorbent core production systems are unable to adequately synchronize the line speed with the deposition rate of the SAP 326 during periods of transition, such as ramp-up and ramp-down. As a result, the core composites 348 produced during these transitory periods often have undesirable and/or non-uniform concentrations of SAP 326 and typically are discarded as waste. If the deposition rate of the SAP 326 leads the line speed, then more SAP 326 often is deposited in the core composite 348 than desired, resulting in a waste of SAP 326. Likewise, if the deposition rate of SAP 326 lags behind line speed, then less SAP 326 often is deposited than desired, which can result in a quality control rejection of the core composite 348 produced during these transitional periods. Either way, material, time, and effort may be wasted. Accordingly, the present invention eliminates or substantially minimizes the potential waste during these transitional periods.

Figure 17:
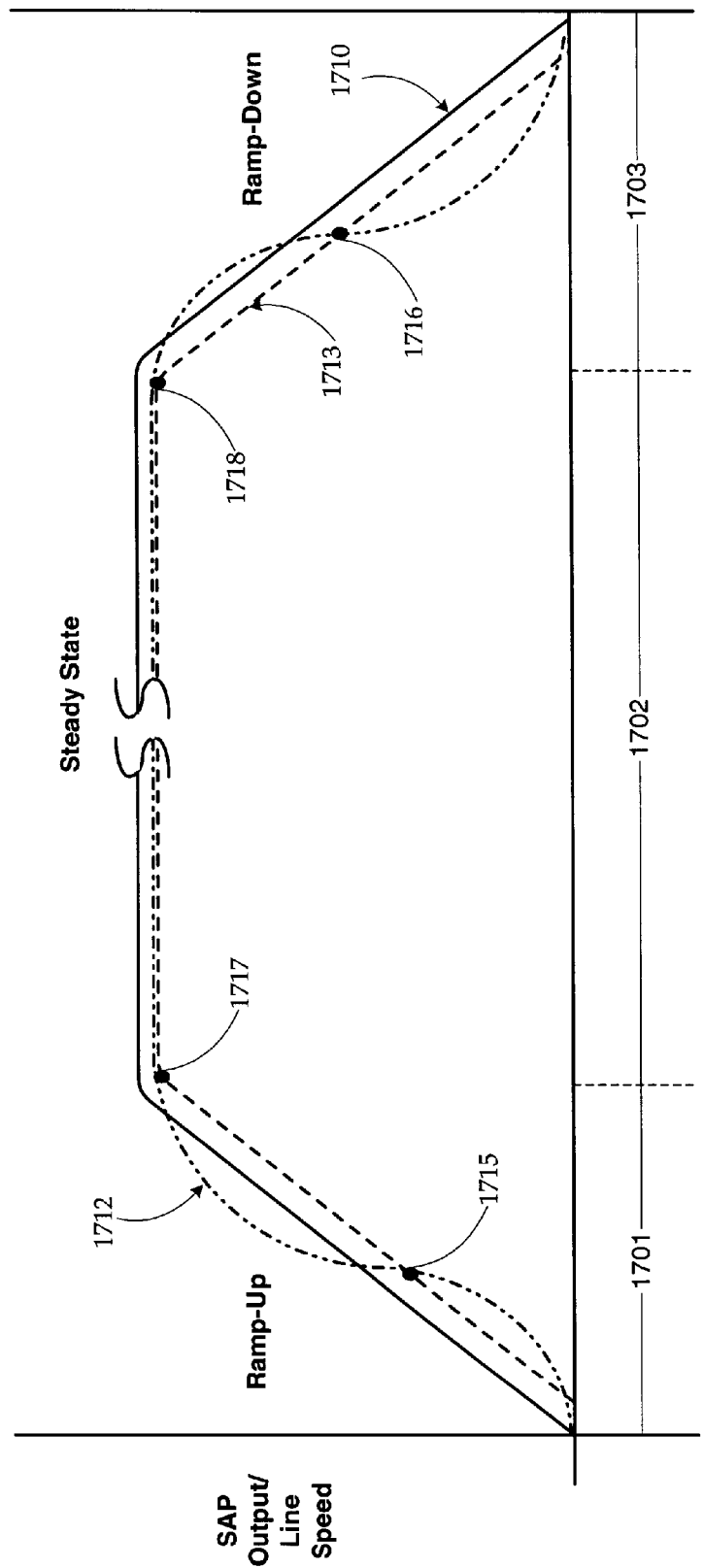
FIG. 17 is a chart illustrating a response of a feedback control system during transitional periods in accordance with a preferred embodiment of the invention when compared to a response of a known system.

FIG. 17 shows an exemplary line speed curve 1710 of the vibratory feeder 332 over time overlaid with an exemplary conventional SAP deposition response 1712 of known systems and an exemplary improved SAP deposition response 1713 of the present invention. The ordinate of the graph illustrated in FIG. 18 represents the deposition rate of SAP 326, such as grams/second, for the conventional SAP deposition response 1712 and the improved SAP deposition response 1713. With respect to line speed curve 1710, the ordinate represents the line speed (the rate of conveyance of fibrous material, preferably opened tow 312, for example), such as in feet/second. The abscissa represents a time span where the line speed of the vibratory feeder 332 goes from a standstill to a steady state back to a standstill.

Ramp-up period 1701 includes the time period from when vibratory feeder 332 goes from a stand-still to a steady state speed; ramp-down period 1703 represents the time period when the vibratory feeder 332 transitions from a steady state line speed to a stand-still; and steady state period 1702 represents the time period between ramp-up period 1701 and ramp-down period 1703 wherein the assembly line and the vibratory feeder 332 operates are a substantially constant line speed. The term "ramp-up," as used herein, refers to the period during which the line speed transitions from a low (or zero) line speed to a high line speed. Likewise, the term "ramp-down," as used herein, refers to the period during which the line speed of the vibratory feeder 332 transitions from a high line speed to a low (or zero) line speed. Although the present invention is not limited to any specific ramp-up or ramp-down time periods, the ramp-up and ramp-down typically takes between 10 to 20 seconds.

The line speed curve 1710 illustrates an example of the line speed of the vibratory feeder 332 (i.e., the rate at which opened tow 312 as it is conveyed past the vibratory feeder 332) over time from ramp-up to ramp-down. During ramp-up period 1701, the line speed of the vibratory feeder 332 increases at a substantially linear rate. During steady-state period 1702, the line speed is relatively constant, and the line speed decreases at a substantially linear rate during ramp-down period 1703. In general, known SAP feeders have difficulty matching the rate of increase of the line speed due to certain factors, such as the capability of the control system to quickly adapt to the changing line speed. Likewise, if parameters of the known SAP feeder are changed, such as the type or properties of the SAP material, typically there is no way for the operation of the control system of these SAP feeders to automatically adapt to the parameters and feed material accordingly. The known SAP feeders generally are unable to deposit SAP 326 at a rate substantially proportionate to the line speed at any given time during ramp-up and ramp down because of these shortcomings.

It will be appreciated that a mismatch in the SAP deposition and the line speed can result in a less than desirable concentration of SAP 326. For example, if desired concentration of SAP 326 is 20 grams/linear centimeter (cm) and the line speed is 10 linear cm/second (s), then the SAP deposition rate should be 200 grams/s to achieve the desired concentration. However, if a SAP deposition rate of only 180 grams/s were achieved, then the actual concentration would be only 18 grams/cm. Likewise, if 220 grams/s of SAP 326 were deposited, the SAP concentrations would be 22 grams/cm. Accordingly, it will be appreciated that it often is desirable to maintain a SAP deposition rate proportionate to the line speed to minimize waste. For example, if a typical ramp-up or ramp-down period is 20 seconds and absorbent cores are manufactured at a rate of 300 cores/minute, then there is the potential for 100 absorbent cores to be rejected for non-conformance during each ramp-up or ramp-down period due to undesirable concentrations of SAP 326.

To illustrate, in this example, the core composite 348 produced before point 1715 or after point 1716 by conventional SAP feeders would receive less SAP 326 than desired because the SAP deposition rate would be below an ideal SAP deposition rate proportionate to the line speed. As a result, the core composite 348 produced during these periods would typically be rejected. On the other hand, the core composite 348 manufactured after point 1715 and before point 1717 and after point 1718 and before point 1716 would receive more SAP 326 than desired, resulting in a waste of SAP 326.

To synchronize the deposition rate of SAP 326 with the line speed during ramp-up and ramp-down, the present invention preferably adapts the control system 320 to adjust the deposition rate of the SAP 326 so that the SAP deposition rate increases/decreases proportionally to the increase/decrease in the line speed during ramp-up and ramp-down transitions.

Figure 16:
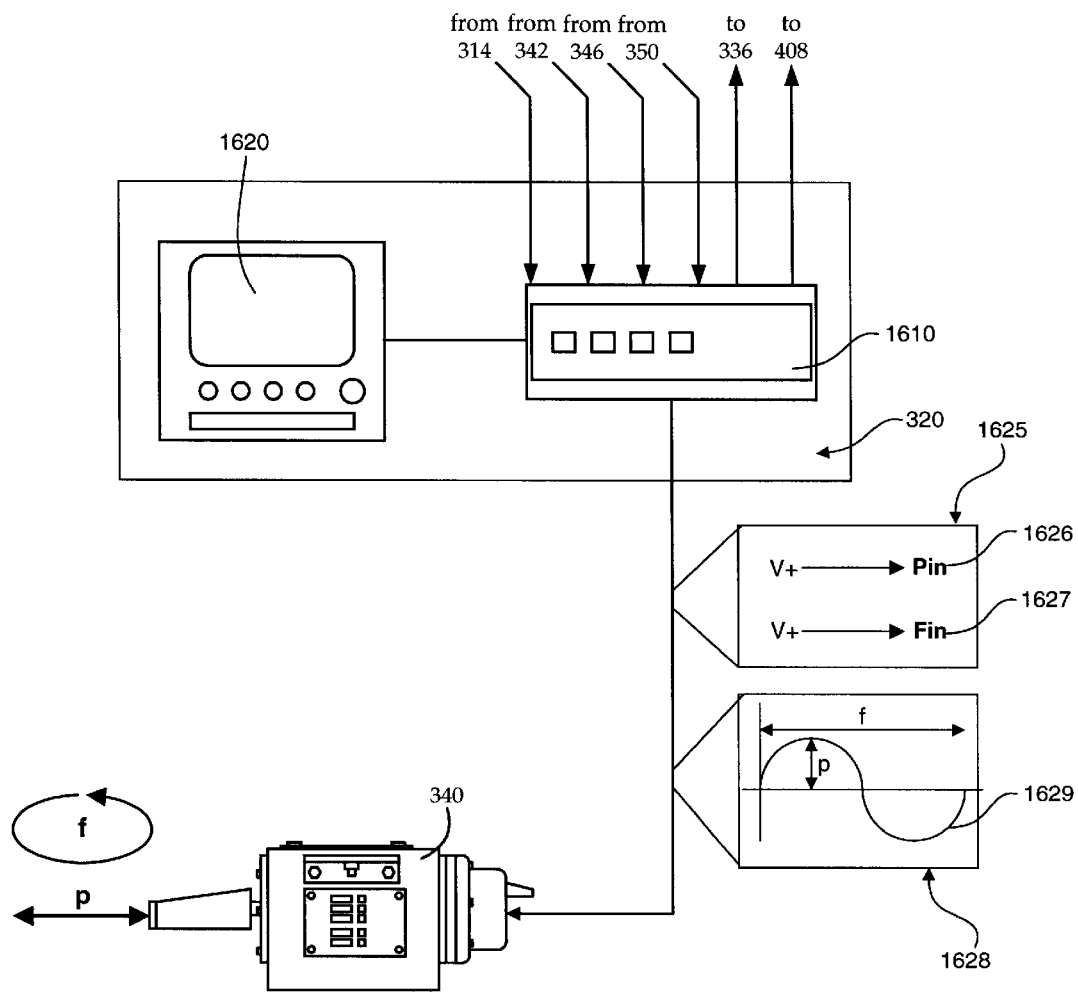
FIG. 16 is a block diagram illustrating a feedback control system in accordance with a preferred embodiment of the present invention.

A PLC device, such as the PLC device 1610 of FIG. 16, is advantageous over other types of control systems since PLC devices generally have a faster response time to a stimulus, and are therefore capable of executing many more control feedback cycles during a certain time period compared to other control system devices. Likewise, PLC devices generally are vendor-independent, and therefore often can be programmed to adapt to different parameters of the vibratory feeder 332. Accordingly, using a PLC device, such as the PLC device 1610 shown in FIG. 16, the change in the SAP deposition rate of the vibratory feeder 332 can be more precisely synchronized with the change in the line speed, as shown with improved SAP deposition response 1713. As illustrated, the SAP deposition rate increases at the same rate that the line speed increases during ramp-up period 1701 and decreases at the same rate during ramp-down period 1703. As a result, the concentration of SAP 326 remains substantially uniform, thereby eliminating or minimizing the amount of SAP 326 and/or core composite 348 wasted.

Referring now to FIGS. 18–19, a method of synchronizing the SAP deposition rate with the line speed of the vibratory feeder 332 during ramp-up is illustrated in accordance with one embodiment of the present invention. In one embodiment, the line speed response of the vibratory feeder 332 is predetermined prior to the operation of the vibratory feeder 332 for producing core composite 348. For example, a "dry run" can periodically be performed with the vibratory feeder 332 to determine the line speed response of the vibratory feeder 332. At each specified time interval of the ramp-up period during the dry-run, a value representing the line speed of the vibratory feeder 332 at that time interval can be recorded, such as by using the tachometer 346 shown in FIG. 3. The line speed values for the specified time intervals then can be provided to the control system 320 for use in synchronizing the SAP deposition rate with the line speed. The line speed values can be provided as a database in file indexed by time interval, correlated to a mathematical equation or algorithm that can be implemented by the control system 320, and the like. Those skilled in the art can develop mechanisms to provide information representing the line speed to the control system 320, using the guidelines provided herein.

An exemplary line speed response during ramp-up is illustrated as the ramp-up line speed curve 1801. The abscissa represents the ramp-up time period, such as ramp-up period 1701 of FIG. 17 and the ordinate represents the line speed, such as in feet/second. The ramp-up line speed curve 1801 can be provided to the control system 320 as data in a file or data structure, implemented as an algorithm, and the like. For illustrative purposes, the ramp-up period (i.e., the time from start-up to steady state operation), as shown, includes ten one-second intervals for a total ramp-up time period of ten seconds.

As discussed above, it generally is beneficial for the SAP deposition rate to follow the line speed of the vibratory feeder 332 to provide a steady concentration of SAP 326 to the core composite 348. Accordingly, in at least one embodiment, SAP deposition rates proportionate to the measured line speeds values 1811–1820 can be determined for specified time intervals of the ramp-up period. The ramp-up SAP deposition curve 1804 is an exemplary illustration of a SAP deposition rate curve corresponding to the ramp-up line speed curve 1801 during ramp-up. As illustrated, the ramp-up SAP deposition curve 1804 includes SAP deposition rate values 1821–1830 corresponding to the line speed values 1811–1820 for their respective time intervals. In general, the magnitude of the deposition rate values 1821–1830 of ramp-up SAP deposition curve 1804 increase at substantially the same rate of increase as the corresponding line speed values 1811–1820 of the ramp-up line speed curve 1801. As illustrated, ramp-up line speed curve 1801 is substantially linear and increasing at a certain rate, and the ramp-up SAP deposition curve 1804 is substantially linear and increasing at the same rate. Since the increase in the SAP deposition rate is proportionate to the increase in the line speed, the vibratory feeder 332 provides a constant concentration of SAP 326.

A preferred method of determining the SAP deposition values 1821–1830 for specified time intervals during the ramp-up period includes converting the corresponding line speed value into a SAP deposition rate value using a desired SAP concentration. For example, if the desired SAP concentration is a uniform 20 grams of SAP/ft and the line speed value during the first second of the ramp-up period (line speed value 1811) was determined previously to be 2 ft/s, then the corresponding desired SAP deposition rate value 1821 would be a value of 40 grams SAP/s. Likewise, if the line speed at the fourth second of the ramp-up (line speed value 1814) is 8 ft/s, then the SAP deposition rate value 1824 would be 160 grams SAP/s. In other words, the line speed values 1811–1820 can be multiplied by a constant conversion value to generate the corresponding SAP deposition rate values 1821–1830. Those skilled in the art can develop other methods of correlating the desired SAP deposition rate with the line speed of the vibratory feeder 332, using the guidelines provided herein.

Using the ramp-up SAP deposition curve 1804, one or more desired properties of the vibratory motion of the vibrator 340 can be determined for each specified time interval of the ramp-up period. Recall that the properties (i.e., the pitch and/or frequency) of the vibratory motion of the vibrator 340 preferably are manipulated to modify the SAP deposition rate of the feed tray 334. The ramp-up pitch response curve 1802 illustrates the necessary pitch of the vibrator 340 over the ramp-up period to generate the corresponding SAP deposition rate illustrated by ramp-up SAP deposition curve 1804. For example, for the first one-second interval of the ramp-up period, a pitch of 10 micrometers ($\mu$m) (pitch value 1831) could be determined to cause a SAP deposition rate of 20 grams SAP/s (SAP deposition rate 1821), while a pitch of 25 $\mu$m (pitch value 1832) is necessary to generate a SAP deposition rate of 40 grams SAP/s (SAP deposition value 1822).

In some cases, the increase in the pitch/frequency of the vibrator 340 may not be proportionate to the increase in the SAP deposition rate. At lower SAP deposition rates, it has been found that a disproportionate pitch and/or frequency may be needed for the vibratory feeder 332 to accurately deposit SAP 326. Likewise, the feeder tray 334 may be absent of SAP 326 when the vibratory feeder 332 is first started. In this case, it may be necessary to quickly increase the pitch and/or frequency to quickly fill the feeder tray 334 with SAP 326.

The pitch values 1831–1840 can be determined based on experimentation, derived from an algorithm or function describing the motion of SAP 326 in the vibratory feeder 332, and the like. As with the line speed values 1811–1820, the pitch values 1831–1840 can be represented as data in a file or database, as an algorithm or function, and the like. In a preferred embodiment, the pitch values 1831–1840 are determined by experimentation and testing. In this case, the vibratory feeder 332 is operated throughout the pitch range of the feeder 332 and the output for each pitch is recorded through measurement in loss in weight of the vibratory feeder 332. Those skilled in the art can develop methods to correlate one or more properties of the vibratory motion of the vibrator 340 to generate a desired deposition rate, using the guidelines provided herein.

FIG. 19 illustrates a method to control the vibratory motion of the vibrator 340 to affect a desired SAP deposition rate during ramp-up. In a preferred embodiment, the control system 320 uses the predetermined ramp-up pitch response curve 1802 (or representative data thereof) to control the SAP deposition rate of the vibratory feeder 332 via the vibratory motion of the vibrator 340. As discussed previously, in one embodiment, a line speed response of the vibratory feeder 332 (ramp-up line speed curve 1801) is previously determined and assumed to be substantially similar for subsequent ramp-up periods. For example, the line speed response curve of an absorbent core assembly line may only vary by 1–2%. Since the line speed response curve generally varies little, the ramp-up pitch response curve 1802 during ramp-up can then be predetermined based on a desired ramp-up SAP deposition curve 1804 corresponding to the predetermined line speed response curve 1801.

In a preferred embodiment, the control system 320 uses the ramp-up pitch response curve 1802 to control the pitch of the vibrator 340 at each specified time interval of the ramp-up period. Since the pitch values 1831–1840 were predetermined, through experimentation or theoretical calculation, to result in a corresponding SAP deposition rate when applied to the vibrator 340, the control system 320 can use these pitch values to reach the desired SAP deposition rates during the specified time intervals. For example, at the first second of the ramp-up period, the control system 320 can send a signal to the vibrator 340 to generate a vibratory motion having a pitch of 10 mm (pitch value 1831). The 10 mm pitch of the vibrator 340 causes the feeder tray 334 to deposit SAP at the corresponding rate (SAP deposition rate 1821). Likewise, at the second time interval of the ramp-up, the control system can signal the vibrator 340 to generate a vibratory motion having a pitch of 25 mm (pitch value 1832) to deposit SAP 326 at the desired rate (SAP deposition rate 1822). Accordingly, the control system 320 can alter the pitch of the vibrator 340 to meet predetermined SAP deposition rates proportional to the predetermined line speed rates of the vibratory feeder 332 during the ramp-up period.

It will be appreciated that variances in the operation of the vibratory feeder 332, such as the use of a different type of SAP 326, changes in the structure of the vibratory feeder, and the like, can cause discrepancies between the ideal SAP deposition rate and the actual SAP deposition rate resulting from a certain pitch of the vibrator 340. Accordingly, in one embodiment, the control system 320 preferably uses one or more scales 342 to "fine-tune" the pitch of the vibrator 340 to obtain the desired SAP deposition rate. As noted previously, the scales 342 can provide information regarding the loss-in-weight of SAP 326 from hopper 336 as SAP 326 is deposited by the vibratory feeder 332. This loss-in-weight information represents the actual deposition rate of SAP 326 and can be compared with the desired SAP deposition rate to determine if there is a difference between the actual deposition rate and the predicted SAP deposition rate associated with a certain pitch. If a discrepancy is detected, then the control system 320 can increase or decrease the pitch of the vibrator 340 accordingly to correct the discrepancy. For example, if a 15 mm pitch of the vibratory motion of the vibrator 340 is predicted to cause the feed tray 334 to deposit 100 grams of SAP 326 per second, but input from the scales 342 to the control system 320 indicate that only 90 grams of SAP 326 actually are being deposited per second, then the control system 320 can use this information to increase the pitch of the vibrator 340 to increase the actual SAP deposition rate to 100 grams/second.

With such a correction mechanism, the length of the time interval used to provide this feedback (i.e., the feedback cycle) is often decisive to the proper operation of the vibratory feeder 322 during transitional periods. If too long of a time interval is used, the alteration of the pitch to correct the SAP deposition rate will lag a change in the line speed, likely resulting in an undesired concentration of SAP 326 in the core composite 348. Accordingly, as the time intervals of the feedback loop decrease, the more likely control system 320 is able to alter the pitch in "real-time." In general, the quicker the response to an incorrect SAP deposition rate, the sooner the error can be corrected and the less SAP 326 and core composite 348 is wasted.

Although a preferred embodiment is described above wherein the control system 320 alters the pitch of the vibrator 340 to control the deposition rate of the vibratory feeder 332, other methods may be used wherein the properties of the vibratory motion of the vibrator 340, such as the frequency, are used in conjunction with, or instead, of the pitch. Using the guidelines provided herein, those skilled in the art can develop such methods with minimal modification.

Figure 20:
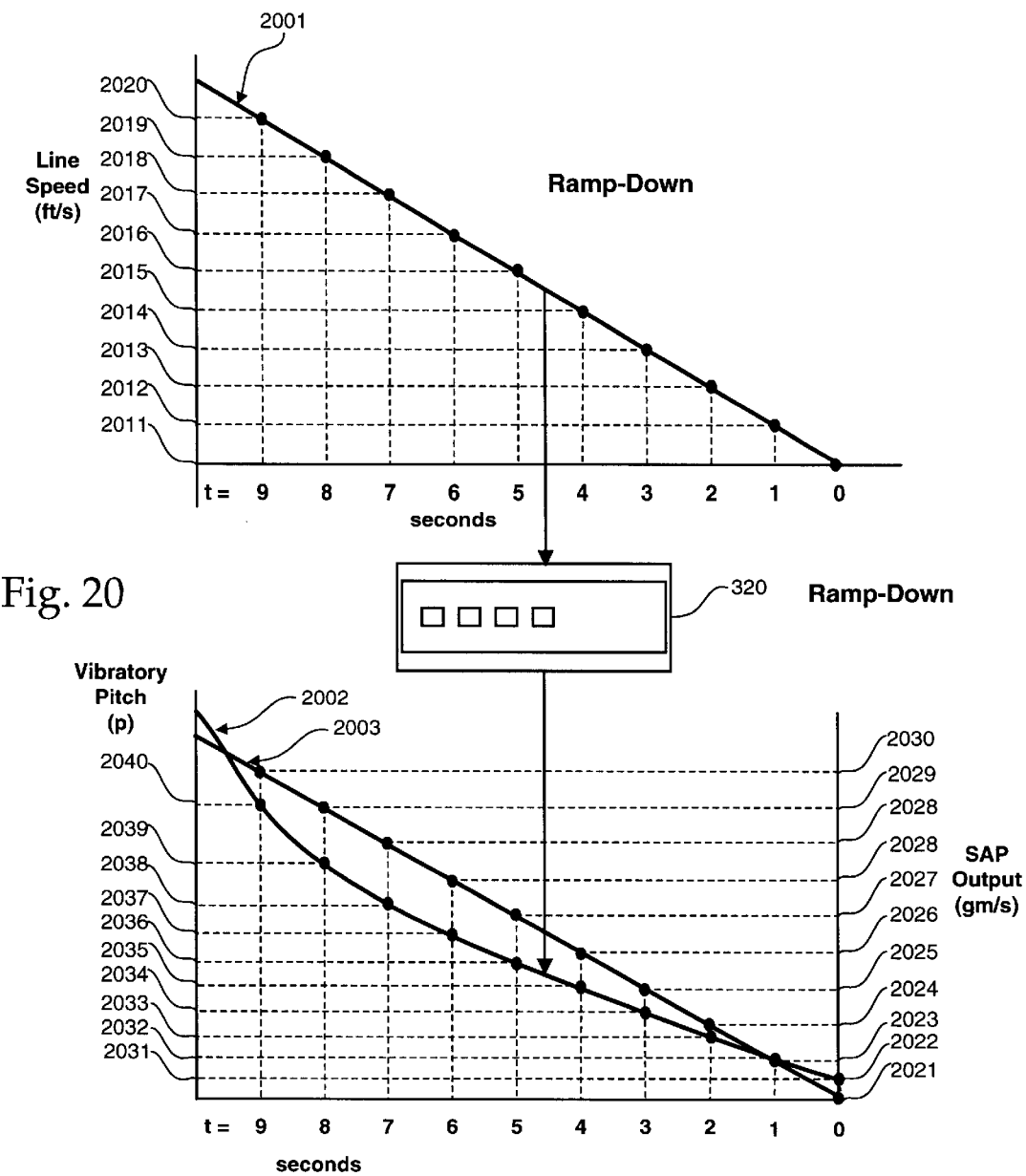
FIGS. 20 and 21 are charts illustrating a method for controlling the deposition of superabsorbent particles during a ramp-up period in accordance with a preferred embodiment of the invention.
Figure 21:
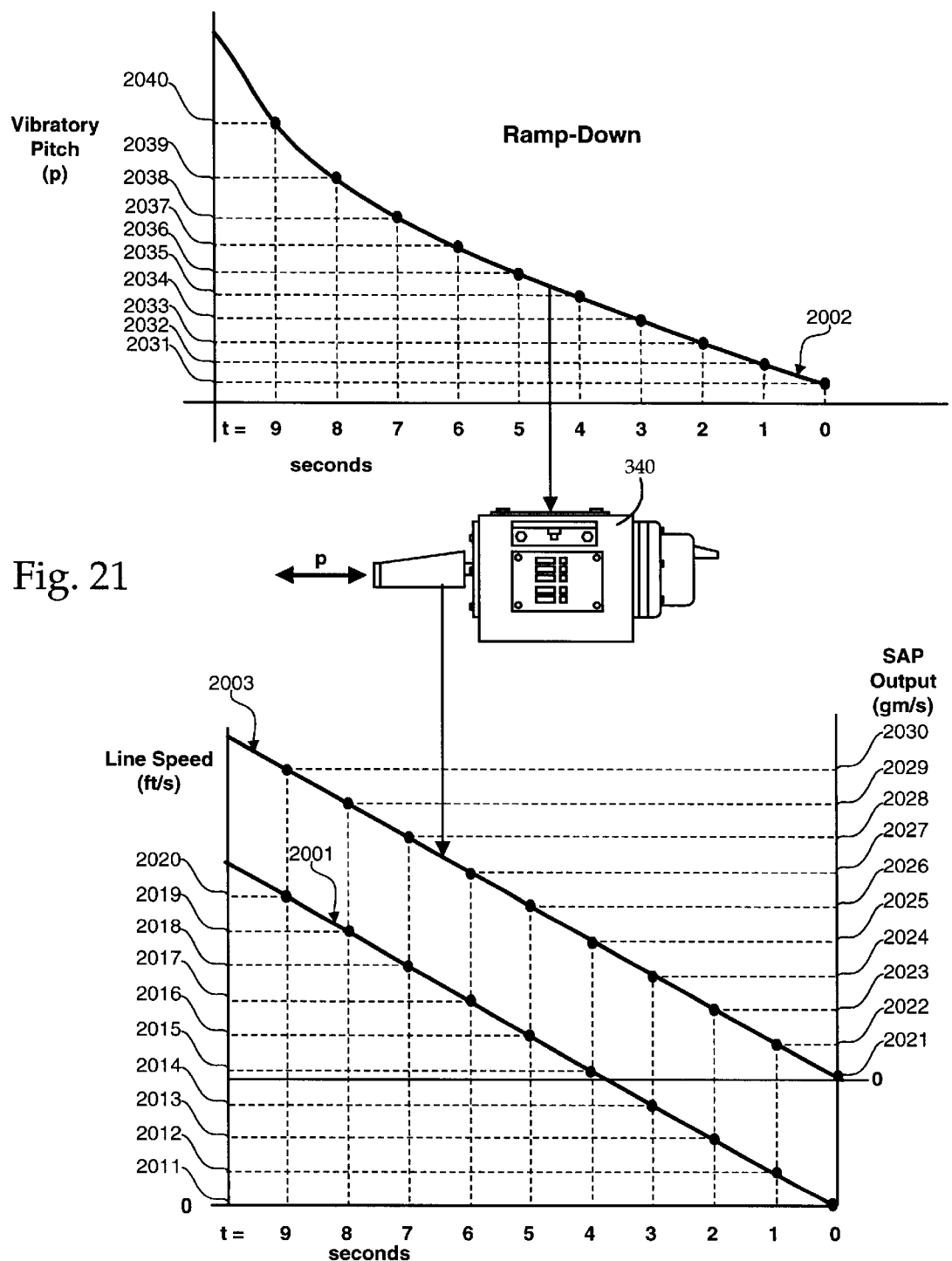

Referring now to FIGS. 20–21, a method to control the deposition rate of SAP 326 during a ramp-down transition is illustrated in accordance with at least one embodiment of the present invention. As discussed above with reference to the ramp-up period, the control system 320 can predetermine the necessary vibratory motion to be performed by the vibrator 340 during each specified time interval of the ramp-down period to result in a substantially uniform SAP concentration along the length of the core composite 348. As with the ramp-up period, an exemplary ramp-down line speed curve 2001 representing the change in line speed of the vibratory feeder 332 during ramp-down can be determined. The line speed values 2011–2020 can be determined by experimentation, such as during a "dry run", they can be calculated, or determined by other mechanisms known to those skilled in the art. For ease of illustration, a ramp-down line speed curve 2001 is illustrated with ten one-second intervals for a total ramp-down period of ten seconds. The corresponding SAP deposition rates 2021–2030 of the ramp-down SAP deposition curve 2003 can be determined based on corresponding ramp-down line speed values 2011–2020, such as by multiplying each ramp-down line speed value by a conversion factor.

The pitch of the vibrator 340 needed to affect the desired SAP deposition rate value can be determined, through experimentation or calculation, and provided to the control system 320 as pitch values 2031–2040 of the pitch response curve 2002. As during ramp-up, the required pitch of the vibrator 340 may not be proportionate to the desired SAP deposition rate during ramp-down. For example, because the feeder tray 334 generally contains a considerable amount of SAP 326 right before ramp-down, the rate of decrease in the pitch of the vibrator 340 may be less than the decrease in the line speed of the vibratory feeder 332.

The control system 320 can use the pitch values 2031–2040 of the pitch response curve 2002 to control the vibratory motion of the vibrator 340, and hence the SAP deposition rate, as illustrated with reference to FIG. 18. As with the ramp-up control method discussed previously, the predetermined pitch values 2031–2040 can be used by the control system 320 during their corresponding time intervals to synchronize the deposition rate of SAP 326 with the line speed of the vibratory feeder 332 during ramp-down. For example, at the first second of the ramp-down period (i.e., t=9 seconds) the control system 320 can send a signal to the vibrator 340 to cause the vibrator 340 to generate a vibratory motion having a pitch of 50 mm (pitch value 2040) to generate a desired SAP deposition rate of 200 grams SAP/s (SAP deposition rate value 2030), and at the second time interval, a signal representing a desired pitch of 32 mm (pitch value 2039) can be provided to the vibrator 340 to affect a desired SAP deposition rate of 180 grams SAP/s (SAP deposition rate 2025). As with the ramp-up scenario presented above, the control system 320, in one embodiment, can use the loss-in-weight input from one or more scales 342 to adjust the pitch of the vibrator 340 to correct any discrepancy between the desired and actual SAP deposition rate.

It will be appreciated that although linear rates of change in the line speed during ramp-up and ramp-down of the vibratory feeder 332 have been illustrated for ease of discussion, in many cases the vibratory feeder 332 may ramp-up and/or ramp-down at a non-linear rate due to the characteristics of the vibratory feeder 332. Accordingly, the present invention applies equally to such situations and, using the guidelines provided herein, those skilled in the art can develop mechanisms for adapting the SAP deposition rate to non-linear increases in line speed during ramp-up and ramp-down with minimal modification.

It will also be appreciated that the precision of the control system 320 in controlling the SAP deposition rate during ramp-up and ramp-down often is related to the length of time between adjustments by the control system 320. Although one-second time intervals (as illustrated) may provide, in some cases, an adequate feedback response time, in most cases such a length of time between adjustments generally is inadequate. The present invention controls the vibratory motion of the vibrator 340 using time intervals preferably less than about 0.5 seconds, more preferably less than about 0.25 seconds, and most preferably less than about 0.1 seconds.

A decrease in the length, or increase in the number, of the time intervals used generally results in an increased burden on the control system 320 due to the increased number of feedback cycles that may occur during any given period of time. Accordingly, the control system 320 preferably includes a programmable logic control (PLC) device, such as PLC device 1610 of FIG. 16. Benefits provided by many PLC devices include less expense to repair/replace; they are more flexible and can be adapted to different operational parameters more easily than vendor-specific controllers; and they tend to be more robust in environments having considerable vibration, dust, and other effects detrimental to electronic devices.

Other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims and equivalents thereof.

What is claimed is:

1. A method for depositing particulate matter into a supply of fibrous material at a deposition rate substantially proportionate to a line speed of the supply of fibrous material during a transition in the line speed comprising:

determining a first vibratory motion of a vibrator adapted to vibrate a feed tray of a vibratory feeder, the first vibratory motion corresponding to a first deposition rate of particulate matter, wherein the first deposition rate is substantially proportionate to a first line speed of the supply of fibrous material;

providing a first signal representative of the first vibratory motion to the vibrator;

determining a second vibratory motion of the vibrator corresponding to a second deposition rate of particulate matter for a second line speed of the supply of fibrous material, wherein the second deposition rate is substantially proportionate to the second line speed; and providing a second signal representative of the second vibratory motion to the vibrator.

2. The method of claim 1, further including predetermining both the first line speed and the second line speed prior to determining both the first vibratory motion and the second vibratory motion.

3. The method of claim 1, further including predetermining the first deposition rate and the second deposition rate, where the first deposition rate and the second deposition rate are proportional to the first line speed and the second line speed.

4. The method of claim 3, further including determining both the first vibratory motion and the second vibratory motion prior to providing both the first signal and the second signal.

5. The method of claim 1, wherein the transition includes a ramp-up transition.

6. The method of claim 1, wherein the transition includes a ramp-down transition.

7. The method of claim 1, wherein the particulate matter includes superabsorbent polymer particles.

8. The method of claim 1, wherein the vibratory motion is selected from a pitch of the vibrator and a frequency of the vibrator.

9. The method of claim 1, wherein the fibrous material includes opened tow.

10. A method for regulating, during a transition in a rate of supply of fibrous material, a rate of deposition of particulate matter into the supply of fibrous material, the method comprising the steps of:

determining a deposition curve, the deposition curve including a plurality of rates of deposition of particulate matter for each time interval of a plurality of time intervals of the transition, wherein each rate of deposition of the plurality of rates of deposition is substantially proportionate to the rate of the supply of fibrous material during the corresponding time interval; and providing the deposition curve to a programmable logic controller, wherein the programmable logic controller is adapted to use the deposition curve to control a rate of deposition of particulate matter into the supply of fibrous material by a vibratory dry material feeder.

11. The method of claim 10, further including predetermining a plurality of line speed values representative of the line speed during the corresponding the plurality of rates of deposition based on the corresponding line speed value of the corresponding time interval.

12. The method of claim 11, further including predetermining a plurality of vibratory motion values corresponding to the plurality of rates of deposition.

13. The method of claim 12, wherein the deposition rate curve includes the plurality of vibratory motion values.

14. The method of claim 10, wherein the transition includes a ramp-up transition.

15. The method of claim 10, wherein the transition includes a ramp-down transition.

16. The method of claim 10, wherein the particulate matter includes superabsorbent polymer particles.

17. The method of claim 10, wherein the vibratory motion is selected from a pitch of the vibrator and a frequency of the vibrator.

18. The method of claim 10, wherein the fibrous material includes opened tow.

* * * * *